United States Patent
Maltby et al.

[11] Patent Number: 5,987,994
[45] Date of Patent: *Nov. 23, 1999

[54] ULTRASONIC METHOD FOR MATERIAL MONITORING

[75] Inventors: Frederick L. Maltby, Jenkintown; L. Jonathan Kramer, Warminster; Glen Mitchell, Dresher, all of Pa.

[73] Assignee: Drexelbrook Engineering Company, Horsham, Pa.

[*] Notice: This patent is subject to a terminal disclaimer.

[21] Appl. No.: 09/048,606

[22] Filed: Mar. 26, 1998

Related U.S. Application Data

[63] Continuation of application No. 08/653,623, May 24, 1996, Pat. No. 5,760,309.

[51] Int. Cl.⁶ .................................................. G01F 23/28
[52] U.S. Cl. ............................ 73/646; 73/290 V; 73/597
[58] Field of Search .......................... 73/597, 612, 618, 73/290 V, 602, 646; 340/612, 618, 621; 364/506, 508, 562

[56] References Cited

U.S. PATENT DOCUMENTS

| | | | |
|---|---|---|---|
| 3,894,431 | 7/1975 | Muston et al. | 73/194 A |
| 4,279,157 | 7/1981 | Schomberg et al. | 73/618 |
| 4,299,128 | 11/1981 | Gruber | 73/627 |
| 5,266,953 | 11/1993 | Kelly et al. | 364/569 |
| 5,392,257 | 2/1995 | Gilmour | 367/135 |
| 5,760,309 | 6/1998 | Maltby et al. | 73/646 |

*Primary Examiner*—Michael Brock
*Assistant Examiner*—Helen C. Kwok
*Attorney, Agent, or Firm*—Reed Smith Shaw & McClay

[57] ABSTRACT

An ultrasonic measurement method in an ultrasonic measurement system having an ultrasonic transducer includes emitting an ultrasonic pulse from the ultrasonic transducer. An ultrasonic pulse is received in accordance with a pulse travel time wherein the amplitude of the received ultrasonic pulse varies according to the pulse travel time. A first electrical signal is provided representative of the received ultrasonic pulse wherein the amplitude of the first electrical signal varies in accordance with the pulse travel time. A second electrical signal is provided in accordance with the first electrical signal wherein the amplitude of the second electrical signal is substantially independent of the pulse travel time. In order to determine the second electrical signal variable amplification is applied to the first electrical signal in accordance with the travel time. A distance is determined according to the pulse travel time wherein the distance is representative of the distance between the transducer and a material surface.

42 Claims, 16 Drawing Sheets

ULTRASONIC METHOD FOR MATERIAL MONITORING

This application is a continuation of application Ser. No. 08/653,623 filed May 24, 1996, now U.S. Pat. No. 5,760,309.

BACKGROUND OF THE INVENTION

1. Field of the Invention

The present invention relates to measurement systems for monitoring various parameters. In particular the present invention relates to ultrasonic parameter measurement systems that operate by emitting and detecting acoustic waves to determine information representing the monitored parameters.

2. Background Art

Ultrasonic instruments have been used to monitor the parameters of materials in a large variety of measuring applications. When the level or height of the surface of a material from the bottom of a container is the parameter to be measured, an ultrasonic instrument can include a transducer for emitting an ultrasonic pulse in the direction of the material and detecting the echo of the ultrasonic pulse reflected from the surface of the material.

The time interval between the emission of the ultrasonic pulse and the detection of the echo of the ultrasonic pulse is determined by the distance between the transducer and the surface of the material. The time interval is measured by the ultrasonic instrument and the measured time is multiplied by the speed of sound to calculate the round trip distance traveled by the ultrasonic pulse. The product of the multiplication can be divided by two to yield the separation between the transducer and the surface of the material and otherwise scaled as desired.

In practice ultrasonic measurement can be complicated by many factors. For example, the speed of sound through a medium is not a constant. The speed of sound varies with the temperature and the composition of the medium through which the ultrasonic pulse travels. Compensating for factors that alter the speed of sound is well known. However, even if the factors altering the speed of sound are not compensated, the effects of the factors are predictable and an uncompensated measurement can be considered approximately correct.

Additionally, it can be difficult to determine when an echo of a transmitted ultrasonic pulse is received by an ultrasonic measurement instrument. Received signals interpreted as a reflected pulse from the material surface by an instrument can be caused by something else in the measuring environment. This can lead to an instrument output that is in error. Furthermore, a received signal can include echo signals returned by a variety of paths. The timing and strength of the various received signals depend upon the path traveled and the materials encountered along the path.

For instance, a received signal can contain an echo from the material surface, or an echo from the bottom of the vessel containing no material, and an echo from an object inside the vessel, such as a pipe. When an ultrasonic measurement instrument receives a strong echo from, for example, a pipe located above the material surface, it can generate an output indicating that the material level is at the level of the pipe. The effects of errors of this nature can be serious. For example, when hazardous materials are involved a critical control action can be undertaken or not undertaken in reliance upon an incorrect indication of material condition.

One method of addressing some of the problems associated with ultrasonic instrument measurement is profiling. In the profiling process, the vessel containing the material to be measured is emptied. Ultrasonic pulses are emitted into the vessel and the echo signals are received. All echo signals received are stored. The stored information can later be used to cancel the spurious echoes.

While the profiling measurement method can improve measurement accuracy, it has several drawbacks. There is substantial expense associated with the electronic systems necessary to acquire, store and compare the data. Furthermore, profiling is cumbersome and time consuming. It is also subject to errors from changes in the measuring environment, such as changes in the material properties or modification of the vessel or its internal apparatus. Any such changes may require that the profiling be repeated.

It is therefore a general object of the present invention to provide an ultrasonic measuring system that avoids the drawbacks of existing ultrasonic measuring systems.

It is another object of the present invention to provide an ultrasonic measuring system that is easily calibrated.

It is another object of the present invention to provide an ultrasonic measuring system with improved measurement accuracy.

It is another object of the present invention to provide an ultrasonic measuring system that is adaptable for use in standard instrumentation signaling and power systems, including two-wire systems and digital signaling systems.

It is another object of the present invention to provide an ultrasonic measurement system which is simple, rugged, reliable and inexpensive.

In accordance with the foregoing objects, the present invention includes a novel system for processing received ultrasonic signals that improves the accuracy of determining when a received signal corresponds to a material condition of interest. The system of the present invention includes means for varying the responsiveness of the received signal processing circuitry as a function of the elapsed time after an ultrasonic pulse is transmitted.

Other objects and features of the present invention will be understood with reference to the drawings, the following description and the appended claims.

SUMMARY OF THE INVENTION

An ultrasonic measurement method in an ultrasonic measurement system having an ultrasonic transducer includes emitting an ultrasonic pulse from the ultrasonic transducer. An ultrasonic pulse is received in accordance with a pulse travel time wherein the amplitude of the received ultrasonic pulse varies according to the pulse travel time. A first electrical signal is provided representative of the received ultrasonic pulse wherein the amplitude of the first electrical signal varies in accordance with the pulse travel time. A second electrical signal is provided in accordance with the first electrical signal wherein the amplitude of the second electrical signal is substantially independent of the pulse travel time. In order to determine the second electrical signal variable amplification is applied to the first electrical signal in accordance with the travel time. A distance is determined according to the pulse travel time wherein the distance is representative of the distance between the transducer and a material surface.

DETAILED DESCRIPTION OF THE INVENTION

Figure 1:
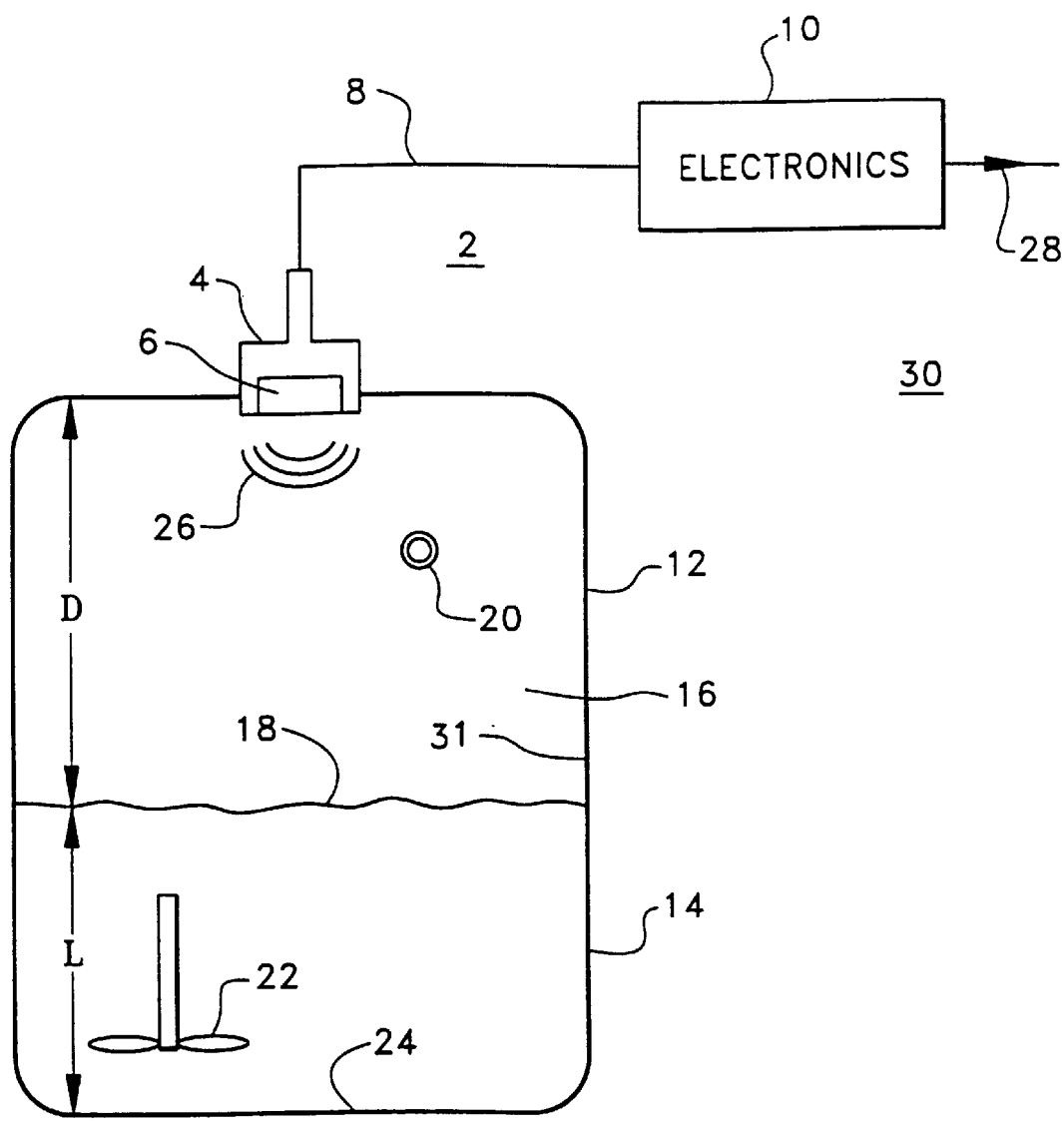
FIG. 1 is a schematic diagram illustrating an ultrasonic measuring environment in which the present invention can be used.

Referring now to FIG. 1, there is shown a schematic diagram illustrating ultrasonic measurement system 30 for making an ultrasonic measurement. An ultrasonic measurement can be made within ultrasonic measurement system 30 either in accordance with the known prior art or in accordance with the system of the present invention. Within ultrasonic measurement system 30 storage tank 12 or storage vessel 12 is used to store material 14 having a material level L. The material level L of material 14 within storage vessel 12 can be the parameter of interest for measurements performed using ultrasonic measurement system 30.

Ultrasonic instrument system 2 is provided within ultrasonic measurement system 30 for determining an output signal on output line 28. The output signal is representative of material level L within storage vessel 12. Instrument system 2 is an ultrasonic instrument system that comprises a sensor 4 and a electrical circuitry 10 coupled to sensor 4, such as by telemonitoring cable 8, in order to permit remote monitoring of electrical circuitry 10. Sensor 4 contains an electroacoustic transducer 6 that is typically an ultrasonic crystal and may be made of barium titanate or lead zirconate or any other material known to be used to form ultrasonic crystals. An ultrasonic crystal for this type of measurement can have a resonant frequency of fifty kilohertz.

Electrical circuitry 10 of instrument system 2 applies an electrical signal to electroacoustic transducer 6 by way of telemonitoring cable 8. The electrical signal applied by electrical circuitry 10 is a short AC burst at a frequency at or near the resonant frequency of electroacoustic transducer 6. The peak voltage of the burst from electrical circuitry 10 can be several hundred volts. Electroacoustic transducer 6 converts the applied electrical signal from electrical circuitry 10 into an acoustic signal. The acoustic signal thus generated is launched into the interior of storage vessel 12 by electroacoustic transducer 6 in the direction of material 14 as ultrasonic pulse 26.

Material 14 is covered by further material 16. Further material 16 can be air, although it can be any other gaseous or liquid material. Ultrasonic pulse 26 travels through further material 16 or air 16 above material 14 and encounters material surface 18 at the interface between air 16 and material 14. At surface 18 of material 14 a reflection of ultrasonic pulse 26 occurs due to the change in the speed of sound at the interface Reflected ultrasonic pulse 26 travels back through air 16 and is returned to transducer 6 as an ultrasonic echo signal or an ultrasonic return signal.

Electroacoustic transducer 6 or ultrasonic transducer 6 converts the ultrasonic return signal reflected from material surface 18 into an electrical signal. The electrical signal from transducer 6 is applied to electrical circuitry 10 by way of cable 8. Electrical circuitry 10 detects the echo-related electrical signal from transducer 6 and determines time T. Time T is the round trip travel time that elapses between the applying of the transducer-energizing electrical signal to transducer 6 and the receiving of the ultrasonic return signal. Because ultrasonic pulse 26 travels distance D between transducer 6 and material surface 18 twice, distance D can be calculated by electrical circuitry 10 from travel time T and the speed of sound R as D=RT/2, wherein the inverse speed of sound can be approximately 1.77 milliseconds/foot.

As previously described, the output of electrical circuitry 10 is provided at output line 28. The signal on output line 28 of electrical circuitry 10 can represent level L of material surface 18. Level L can be calculated by electrical circuitry 10 by subtracting the calculated distance D from the distance of ultrasonic transducer 6 from vessel bottom 24. In alternate embodiments of ultrasonic measurement system 30 other scaling operations can be performed to generate other suitable and useful signals on output line 28 from measured travel time T.

Echo signals reflected from material surface 18 that relate to the parameter of interest are not the only acoustic signals applied to transducer 6 as a result of ultrasonic pulse 26. Echoes from other objects or conditions in the measuring environment are also returned to ultrasonic transducer 6 by a variety of paths as a result of spurious reflections. The spurious reflections cause spurious electrical signals within electrical circuitry 10 that complicate the measurement of distance D within storage vessel 12.

Additionally, objects within storage vessel 12 such as pipe 20 and agitator 22 can cause spurious reflections of ultrasonic pulse 26. The strength and timing of the spurious reflections of ultrasonic pulse 26 can vary widely. When surface level 18 is below the reflecting object, the strength and timing can be generally constant. However, when material surface 18 is above the reflecting object, the strength and timing of the reflected signal can vary with distance D. Discontinuities in vessel walls 31 can also cause reflections with similar properties.

Additionally, vessel walls 31 of storage vessel 12 can also cause spurious echoes. Furthermore, the spurious echoes caused by vessel walls 31 can occur by way of paths involving multiple reflections. An example of such an echo path is the path taken by an ultrasonic pulse 26 reflected from agitator 22, bouncing off vessel walls 30 and returning to transducer 6.

Figure 2:
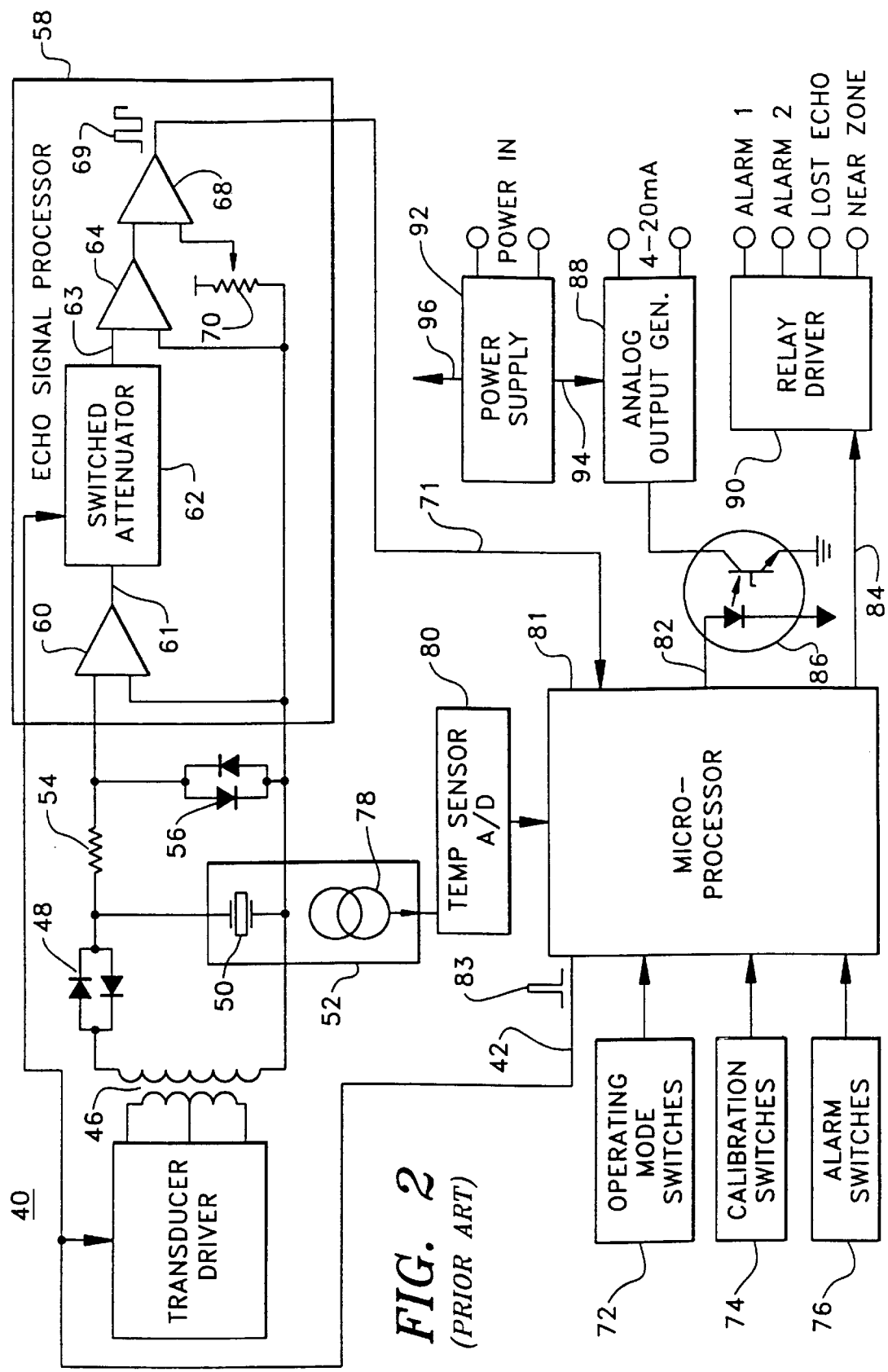
FIG. 2 is a block diagram illustrating a prior art ultrasonic measurement instrument.

Referring now to FIG. 2, there is shown a block diagram representation of prior art ultrasonic measurement system 40 having ultrasonic crystal 50 for performing ultrasonic measurements within ultrasonic measurement system 30. Ultrasonic measurement system 40 operates under the control of microprocessor 81. In order to initiate ultrasonic pulse 26 from ultrasonic crystal 50, microprocessor 81 applies electrical crystal excitation signal 83 including a pulse to excitation line 42. Crystal excitation line 42 is coupled to transducer driver 44 and crystal excitation signal 83 is thus applied to transducer driver 44 by way of crystal excitation line 42. Crystal excitation signal 83 can be a small duty cycle signal wherein the pulse of crystal excitation signal 83 can have a duration of approximately one-hundred microseconds. Crystal excitation signal 83 can have a repetition period of approximately one-hundred to one-hundred forty milliseconds.

A counter or timer is started by microprocessor 81 when microprocessor 81 applies crystal excitation signal 83 to crystal excitation line 42. The timer is used by microprocessor 81 to determine the total travel time of ultrasonic pulse 26. In response to crystal excitation signal 83 of crystal excitation line 42 transducer. Driver 44 generates an ultrasonic AC signal pulse or burst for driving ultrasonic crystal 50 of ultrasonic transducer 6.

A high voltage is induced on the secondary of transformer 46 because of the sharp change in the voltage level of the pulses within excitation signal 83 that are applied to the primary of transformer 46 by microprocessor 81. For this reason the ultrasonic burst can have a voltage amplitude between three hundred volts and four hundred fifty volts peak-to-peak at the secondary of transformer 46. The frequency of the ultrasonic burst can be fifty kilohertz. However, it will be understood that any acceptable frequency range and voltage amplitude can be used for driving ultrasonic crystal 50.

The burst signal on the secondary of transformer 46 is applied as a drive pulse to crystal 50 which is part of ultrasonic sensor 52. The fifty kilohertz drive pulse is applied to ultrasonic crystal 50 by way of diodes 48. Diodes 48 conduct the high voltage drive pulse from transformer 46 but are nonconductive after the high voltage drive pulse has decayed. Diodes 48 thus prevent transformer 46 from loading down the echo-responsive signals from ultrasonic crystal 50. In an alternate embodiment of ultrasonic measurement system 40 with an LC circuit (not shown) tuned to the frequency of ultrasonic crystal 50 can be provided.

When ultrasonic pulse 26 reflects from a surface such as material surface 18 and is applied to transducer 6 it is converted into electrical signals by crystal 50. The electrical signals formed by crystal 50 in this manner can be in the millivolt, or even microvolt, range. They are applied to the input of echo signal processor 58 by way of a voltage limiting circuit that includes resistor 54 and diodes 56. The voltage limiting circuit protects echo signal processor 58 from the high voltage drive pulse of the secondary of transformer 46 used to excite crystal 50 during the initiation of ultrasonic pulse 26. Resistor 44 limits the current applied to echo signal processor 58 and diodes 56 clamp the voltage applied to echo signal processor 58 to approximately seven tenths of a volt during the initiation of ultrasonic pulse 26, while permitting the much smaller echo-representing signals from crystal 50 to pass.

Echo signal processor 58 processes the echo-representing signals from ultrasonic crystal 50 and generates detect signal 69 on detect line 71 in response to the echo-representing signals. Detect signal 69 is representative of the distance D between ultrasonic transducer 6 and material surface 18. The operations of echo signal processor 58 for determining detect signal 69 can be implemented using a variety of analog and digital functional blocks and a variety of different types of circuitry well understood by those skilled in the art.

Echo signal processor 58 of ultrasonic measurement system 40 can include input amplifier 60, switched attenuator 62, amplifier 64 and detector 68 for processing the electrical signals representing ultrasonic pulse 26. It will be understood by those skilled in the art that ultrasonic pulse 26 generated by transducer 6 is not an ideal signal. It requires a substantial rise time in order to reach its peak amplitude as excitation energy is applied to ultrasonic crystal 50 by transformer 46. Additionally, ultrasonic crystal 50 has a decay or a ring down time as stored energy is released from it after excitation of crystal 50 and after the peak response of crystal 50. The ring down signal of ultrasonic crystal 50 can decay exponentially.

Therefore, in the preferred embodiment of echo signal processor 58 input amplifier 60 is adapted to provide low noise high gain to the small signal received from transducer 6 prior to processing by switched attenuator 62. Switched attenuator 62 is adapted to overcome the effect of the ringing down of ultrasonic crystal 50 during measurements performed by ultrasonic measurement device 40. Amplifier 64 is adapted to further amplify the signal provided by transducer 6, and to perform a voltage shift. These operations make detect signal 69 suitable for processing by conventional logic circuitry.

An echo signal reflected from material surface 18 close to transducer 6 has a relatively high amplitude relative to the ring down signal of ultrasonic crystal 50. Thus, if the amplitude of the entire signal received by transducer 6 is lowered by switched attenuator 62, the ring down signal of crystal 50 can be effectively eliminated while the echo signal can remain for processing by switched attenuator 62 and amplifier 64. Therefore, switched attenuator 62 can provide relatively small amplification beginning when excitation pulse 83 initiates excitation of crystal 50, and continue providing relatively small amplification until ringing down has ended. After that period gain provided by switched attenuator 62 can begin to rise. This process is sometimes referred to as time varying gain.

The ringing down problem can also be solved by using a better ultrasonic crystal 50 having a response more closely resembling an ideal response. However, ultrasonic crystals of this quality are too expensive for most ultrasonic measurement applications.

Detector 68 of echo signal processor 58 compares the output of amplifier 64 with the threshold input provided by threshold control circuit 70. The comparison by detector 68 produces detect signal 69 on detect line 71. Detector 68 squares up the input it receives to provide an output suitable for processing by conventional logic circuits. Thus, detector 68 functions, effectively, as an analog-to-digital converter. Detect signal 69 is applied to the interrupt of microprocessor 81 by way of detect line 71 when the processed echo signal level exceeds the threshold input determined by threshold control circuit 70. In general, relatively lower thresholds are preferred to relatively higher thresholds when adjusting threshold control circuit 70. However, if the threshold of circuit 70 is too low echo signal processor 58 becomes too sensitive to noise. A threshold value of 1.3 volts has been found to be suitable.

As previously described, microprocessor 81 includes a timer that is started when crystal excitation signal 83 is applied on crystal excitation line 42. The timer is stopped by microprocessor 83 when detect signal 69 is received from detector 68 of echo signal processor 58 by microprocessor 81. Thus excitation signal 83 and detect signal 69 are used by microprocessor 81 to determine time T between the initiation of ultrasonic pulse 26 and the receiving of a corresponding ultrasonic echo signal. Time T determined in this manner by microprocessor 81 thus represents the round-trip travel time of ultrasonic pulse 26.

In the preferred embodiment of the present invention microprocessor 81 also receives inputs from a variety of input control circuits. The input control circuits can be input control switches in the preferred embodiment of the invention. The input control switches of microprocessor 81 can include operating mode switches 72. Operating mode switches 72 can select from various modes of operation of ultrasonic measurement system 40.

For example, operating mode switches 72 can permit selection of modes such as high level fail safe or low level fail safe, setting measuring units to English or metric, providing time delay and selecting among calibration modes. The control switches coupled to microprocessor 81 can also include calibration switches 74. Calibration switches 74 can be used for setting the zero values and the span or full scale values of storage vessel 12. Alarm switches 76, also coupled to microprocessor 81, can be used for setting levels within storage vessel 12 at which ultrasonic measurement system 40 generates alarm outputs.

Sensor 52 of ultrasonic measurement system 40 can include a temperature sensor 78 for measuring the temperature in the measuring environment of ultrasonic transducer 6. Temperature sensor A/D converter 80 can also be included within ultrasonic measurement system 40 for converting temperature data into digital form for microprocessor 81.

In order to provide a representation of the distance D calculated in accordance with travel time T of ultrasonic pulse 26, microprocessor 81 generates a digital output signal on digital output bus 82. Digital output bus 82 is coupled by way of optoisolator 86 to analog output generator 88. Analog output generator 88 converts the digital signal from optoisolator 86 into an analog form. Analog output generator 88 generates a four to twenty milliamp current output for use in standard indicator devices, controller devices and the like. In standard indicator devices of this type a four milliamp output can indicate, for example, that storage vessel 12 is substantially empty. A twenty milliamp output can indicate that storage vessel 12 is substantially full. Additionally, the output of analog output generator 88 can be applied to a control device (not shown) for controlling the level L material 14 within storage vessel 12.

Microprocessor 81 also provides an output signal on output bus 84 to relay driver 90. Relay driver 90 can generate signals for driving relays to indicate various alarm conditions associated with the measurements performed by ultrasonic measurement system 40. The conditions indicated on output bus 84 can include material conditions exceeding alarm values determined, for example, by alarm switches 76. The conditions indicated on output bus 84 can also indicate conditions below alarm values set by alarm switches 76. For example, the condition indicated on output bus 84 can be that the level of material surface 18 is in the near zone wherein measurements may be less accurate.

The conditions indicated by relay driver 90 can also include a lost echo condition when no threshold-exceeding echo is detected by echo signal processor 58 within a predetermined time after application of crystal excitation signal 83.

Power supply 92 receives input power and provides isolated supply 94 for analog output generator 88. Power supply 92 also provides supply 96 to the remainder of the circuitry of ultrasonic measurement system 40.

Figure 3:
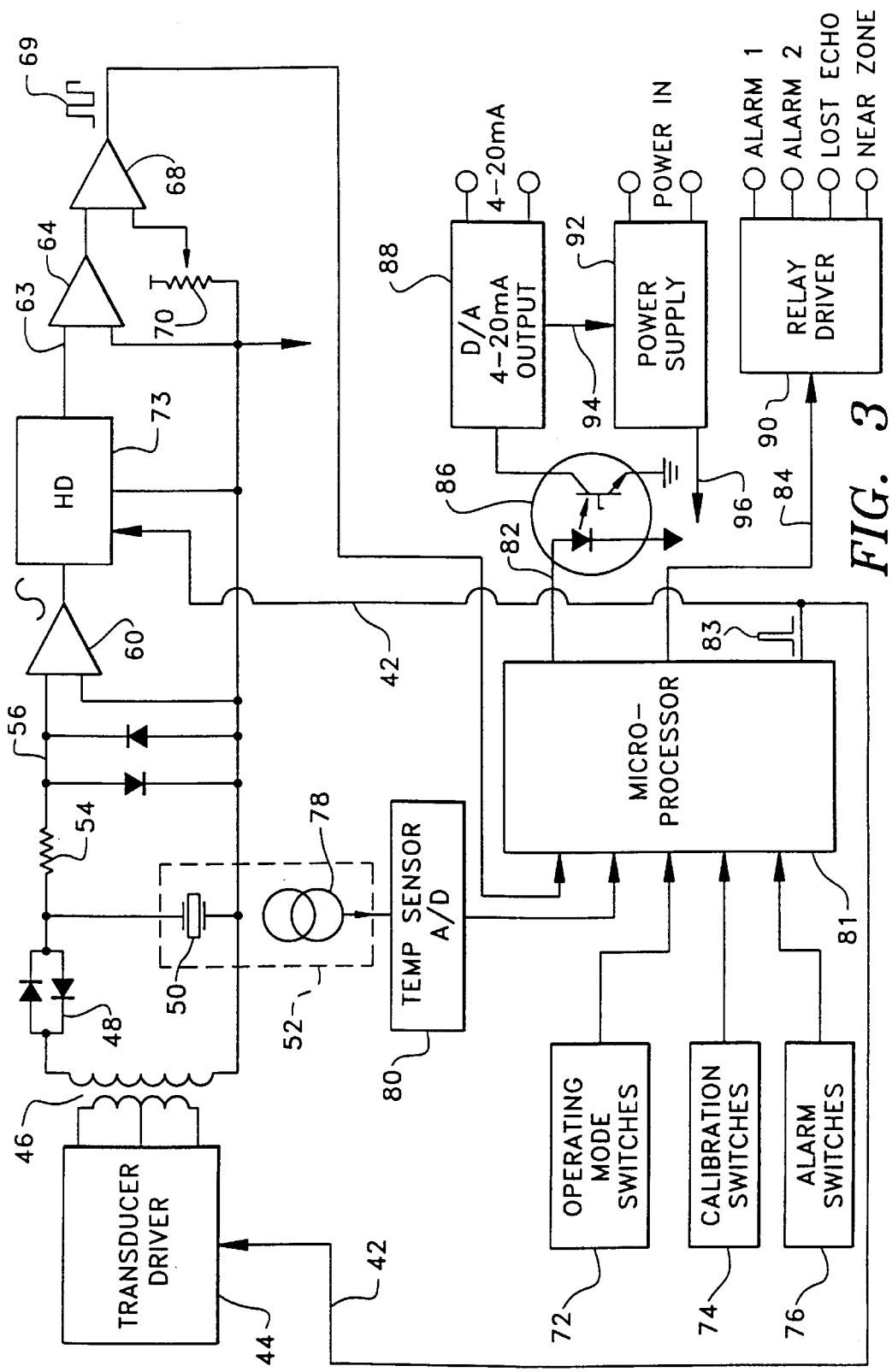
FIG. 3 is a block diagram illustrating the ultrasonic measurement instrument of the present invention wherein a high discrimination variable amplification device is controlled by a microprocessor.
Figure 4:
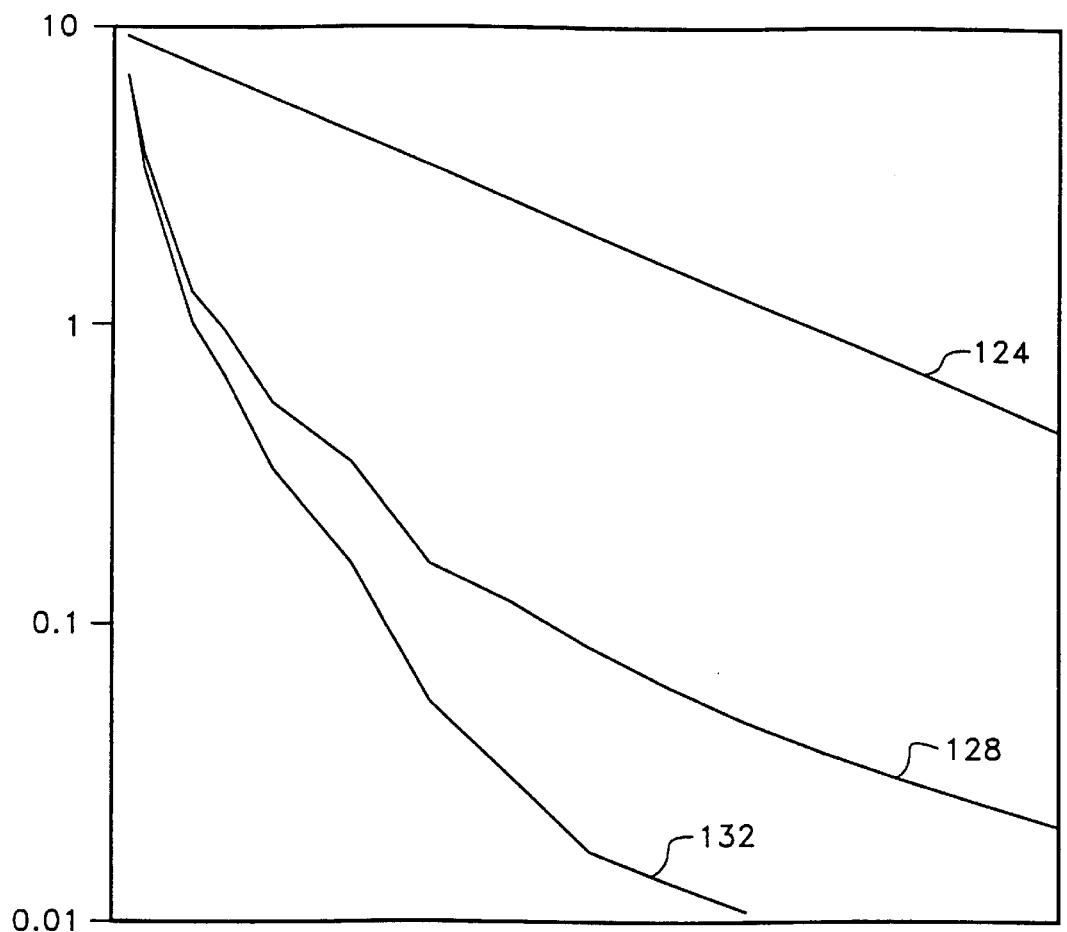
FIG. 4 is a graphical representation of signal strength characteristics which can occur in an ultrasonic measurement instrument such as the ultrasonic measurement instrument of FIG. 3.

Referring now to FIGS. 3, 4, there are shown a block diagram representation of ultrasonic measurement system 75 of the present invention including high discrimination ultrasonic measurement device 73 as well as graphical representation 120. It is understood by those skilled in the art that ultrasonic pulse 26 is attenuated by several effects as it travels along its path from ultrasonic transducer 6, through air 16 to material surface 18, and back to transducer 6 after reflection off material surface 18. In accordance with the method of the present invention ultrasonic measurement system 75 is adapted to compensate for selected attenuation effects in order to provide improved ultrasonic measurements.

One effect that attenuates ultrasonic pulse 26 is a geometric effect wherein pulse 26 is attenuated due to the spreading of the acoustic energy of pulse 26 as pulse 26 travels through a medium. The geometric effect is graphically illustrated by curve 128 of graphical representation 120. The attenuation caused by the geometric effect is substantially an inverse square attenuation, although during the first few feet of pulse travel the pulse behaves as if it is collimated and the attenuation can be somewhat more linear.

Another effect that attenuates ultrasonic pulse 26 is signal loss due to acoustic energy being absorbed by the medium as ultrasonic pulse 26 passes through the medium. This effect is substantially logarithmic and can be measured in dB/meter. This substantially logarithmic effect is represented as curve 124 of graphical representation 120. The substantially logarithmic effect represented by curve 124 is dependent upon the humidity of the air when ultrasonic pulse 26 passes through air. Increased humidity can result in increased attenuation up to a peak attenuation, followed by a decrease in attenuation as humidity increases further. The attenuation caused by the substantially logarithmic effect is also dependent upon the frequency of ultrasonic pulse 26, wherein higher frequencies are attenuated more than lower frequencies by humidity. For example, the attenuation caused by the logarithmic effect can peak at approximately sixty percent humidity for a fifty kilohertz ultrasonic signal.

The result of the substantially inverse square effect and the substantially logarithmic effect operating simultaneously is an echo signal intensity that can diminish by a factor of several thousand as distance D varies, for example, from one foot to forty feet, a desirable span for ultrasonic measurement system 75 to measure. The measured value of the voltage of the response of ultrasonic transducer 6 to the reflected ultrasonic signal can vary accordingly, as indicated by curve 132 of graphical representation 120.

Thus, the amplitude of the electrical signal representing the echo pulse applied to high discrimination ultrasonic measurement device 73 falls off as a function of distance D as illustrated by curve 132. Curve 132 can be determined, for example, by emitting a plurality of ultrasonic pulses 26 for a plurality of differing distances D, preferably over the entire measurement range of storage vessel 12, and measuring, for each pulse, the resulting pulse travel time and the corresponding amplitude of the electrical signal of line 61 or amplitude of the ultrasonic echo signal.

In the method of the present invention measurement device 73 is adapted to provide variable gain to the echo-representing electrical signal of line 61 in order to linearize the electrical signal at the output of device 73 over the entire range of distance D with respect to distance D. The variable gain applied by measurement device 73 is selected to cause the amplitude at the output of measurement device 73 applied to output line 63 to be substantially constant with respect to distance D.

In order to cause the amplitude at the output of measurement device 73 to be substantially constant with respect to distance D while the amplitude of the input follows curve 132, a numerical approximation is made of curve 132. Signals representing the numerical approximation are applied to the gain control of a variable gain device within high discrimination ultrasonic measurement device 73. In this manner measurement device 73 compensates for both the inverse square near zone attenuation represented by curve 128 and the logarithmic attenuation represented by curve 124.

Since the logarithmic effect is dependent upon the relative humidity of the air 16 through which ultrasonic pulse 26 passes, the numerical approximation is performed for a plurality of measurements performed at a selected humidity. In the preferred embodiment of the present invention the selected humidity can be thirty-five percent because thirty-five percent can be an average humidity for measurements made in accordance with the present invention. However, it will be understood that the method of the invention can be advantageously applied to a numerical approximation performed for any values of relative humidity.

Figure 5:
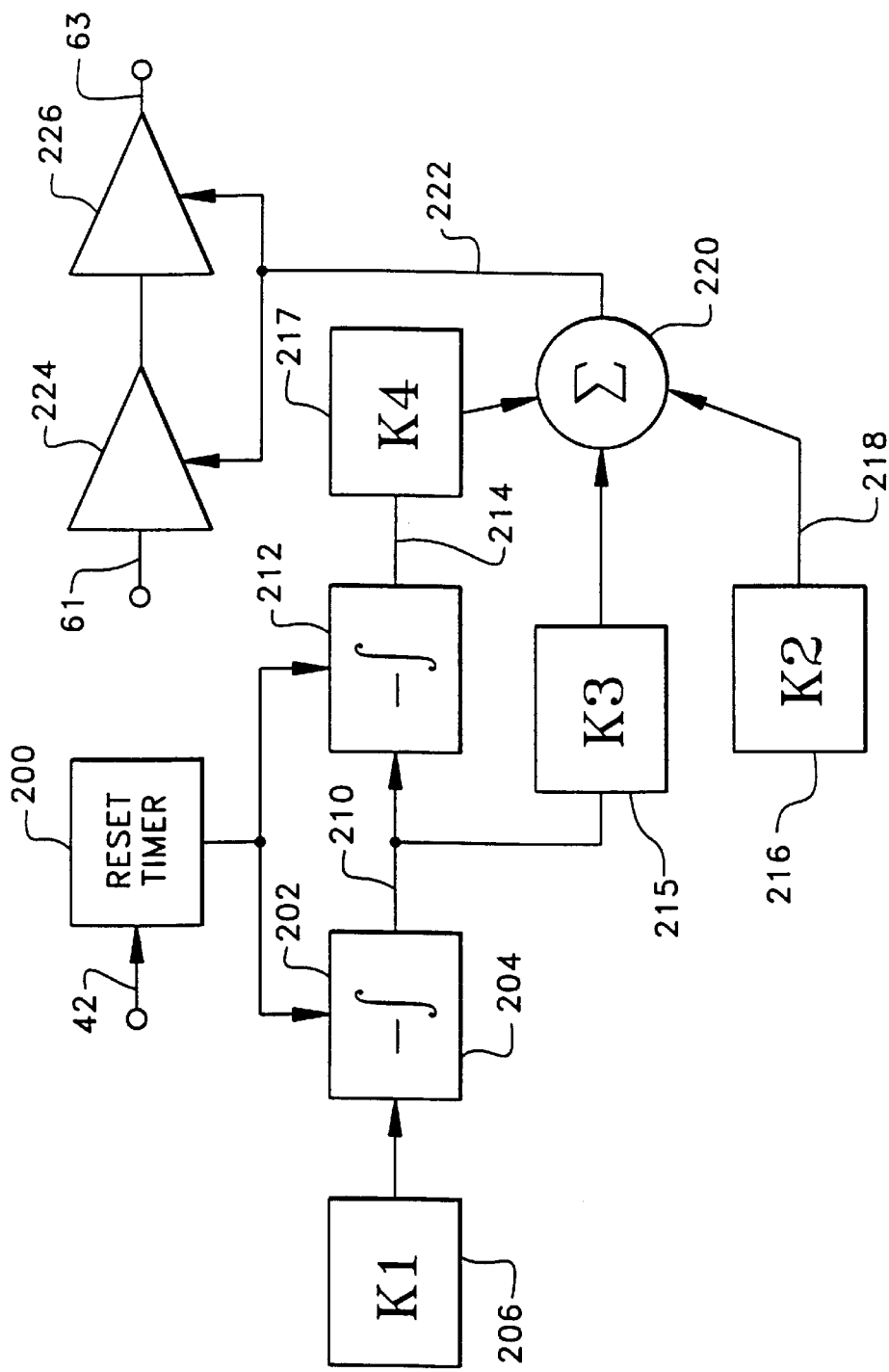
FIG. 5 is a block diagram representation of an integrator for control of a variable amplification device that can be used in an alternate embodiment of the ultrasonic echo signal processor portion of the ultrasonic measurement instrument of FIG. 3.

Referring now to FIG. 5, there is shown a schematic representation of high discrimination circuitry 77 which is a possible embodiment of high discrimination ultrasonic measurement system 71. Within high discrimination circuitry 77 the variable gain suitable for performing the near zone quieting is controlled by integrators 204, 212 rather than microprocessor 81. Integrator 204 receives a constant K1 as its input as shown in block 206. Because the input to integrator 204 is constant, the output of integrator 204, applied to first integrator output line 210, is proportional to time. Integrator 204 begins integrating when it is reset by reset timer 200. Reset timer 200 performs the operation of resetting integrator 204 when it receives the pulse of electrical excitation signal 83 by way of crystal excitation line 42 which is coupled to reset timer 200. Thus the output of integrator 204 at time T is approximately proportional to the elapsed time since the launching of ultrasonic pulse 26 from transducer 6.

Integrator 212 receives the time signal from integrator 204 on first integrator output line 210 and integrates it to provide an output on second integration output line 214. Because the input of integrator 212 is proportional to time, the output on second integrator output line 214 is proportional to time squared. Integrator 212 is also reset by reset timer 200 when the pulse of crystal excitation signal 83 appears on crystal excitation line 42.

The time output of integrator 204 on first integrator output line 210 and the time squared output of integrator 212 on second integrator output line 214 are applied to integrator output summer 220. The two integrator outputs can be provided with constant gains K3 and K4 as shown in blocks 215, 217, respectively. A constant gain offset can also be provided by applying a constant gain K2 to integrator summer 220 as shown in block 216.

The output of integrator output summer 220 is applied by way of gain control line 222 to amplifiers 224, 226. Amplifier 224 receives as its input the output of amplifier 60, by way of line 61. The output of amplifier 60 on line 61 is the echo-representing signal provided by ultrasonic crystal 50. The output of amplifier 224 is applied to amplifier 226 which provides an amplified output on line 63. The gain provided by each amplifier 214, 226 can range from one to thirty. Line 63 is coupled to amplifier 64 which applies its output signal to detector 68.

Because integrators 204, 212 are cascaded their summed output can be represented as a quadratic polynomial. Because the summed output of integrators 204, 212 is applied to the gain control of two cascaded amplifiers 224, 226, the gain at the output of amplifier 226 can be represented as a fourth order polynomial therefore having four break points. The constants of the fourth order polynomial signal at the output of amplifier 226 can be selected by adjusting constants K1, K2, K3 and K4 that are applied to integrators 204, 212.

Ideally a polynomial of a order higher than a fourth order is desirable in order to improve the approximation of curve 132. However, a fourth order polynomial is suitable for approximating curve 132 with acceptance accuracy and making the amplitude of the voltage at the output of amplifier 64 substantially constant with respect to distance D. It will be understood that polynomial approximations of any order other than the fourth order can be provided within the system of the present invention provided the approximation of curve 132 is suitable.

Figure 6A:
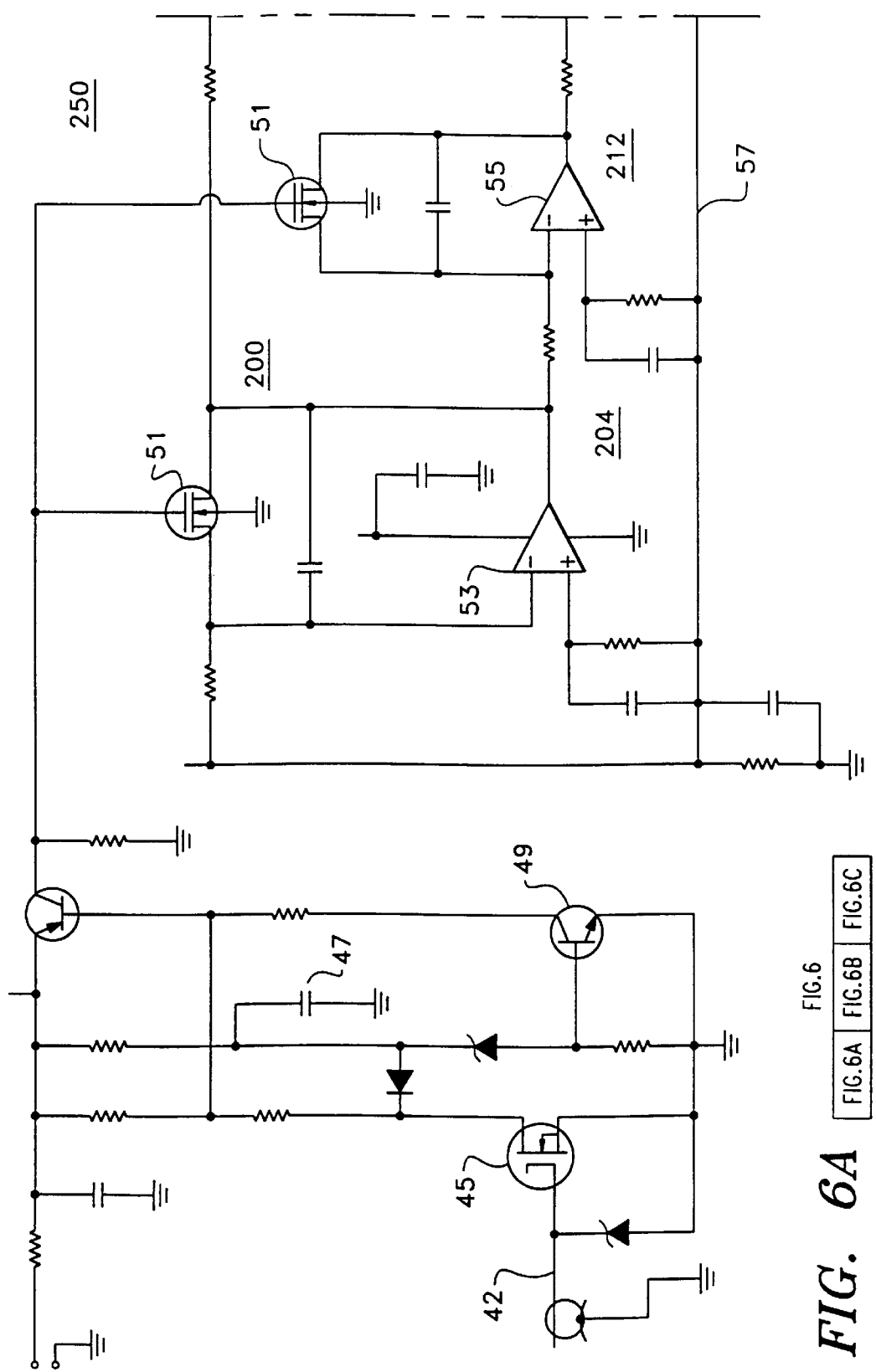
FIGS. 6A, B, C are schematic representations of an ultrasonic echo signal processor suitable for use with the ultrasonic measurement instrument of FIG. 3.
Figure 6B:
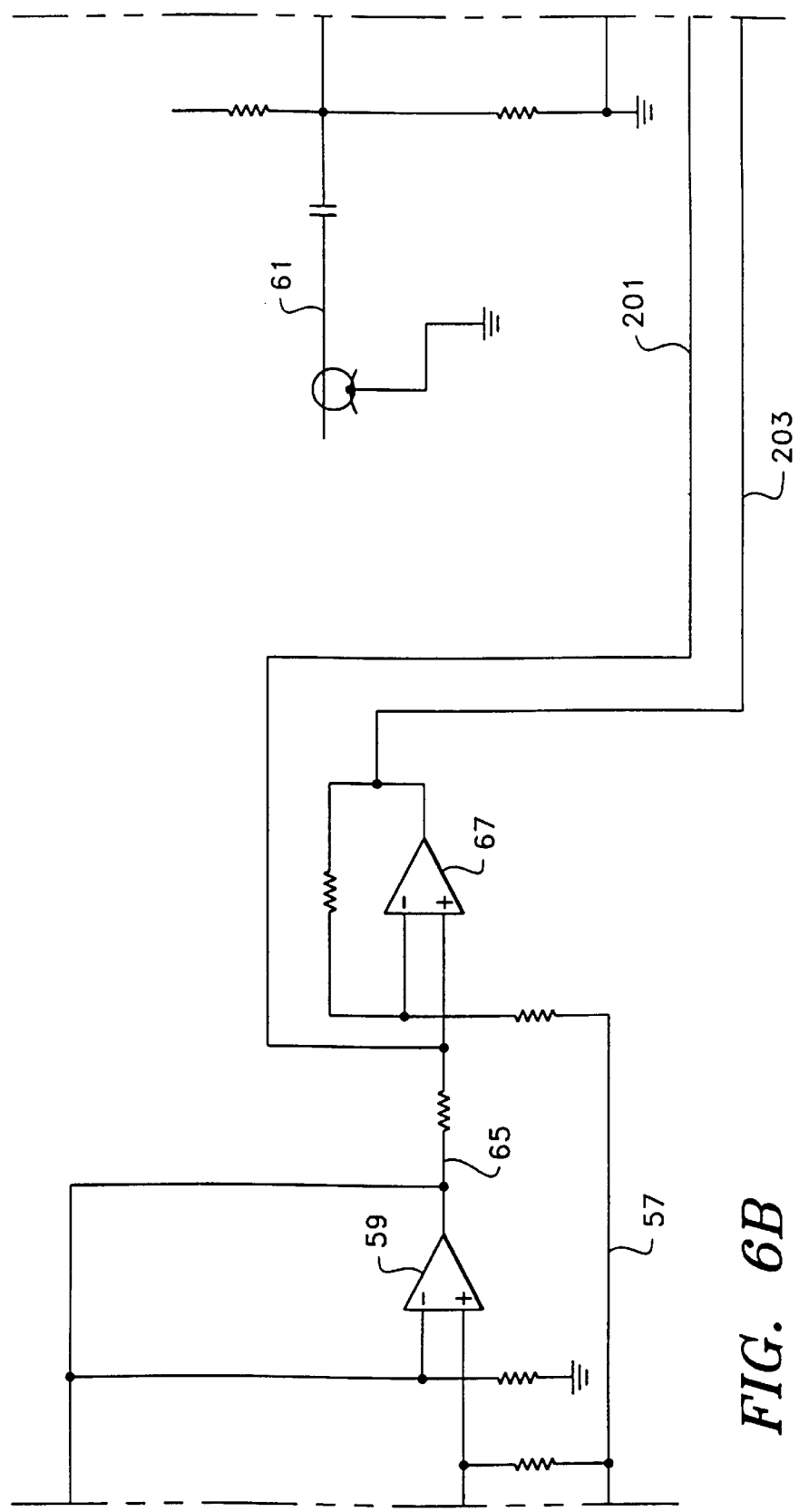
Figure 6C:
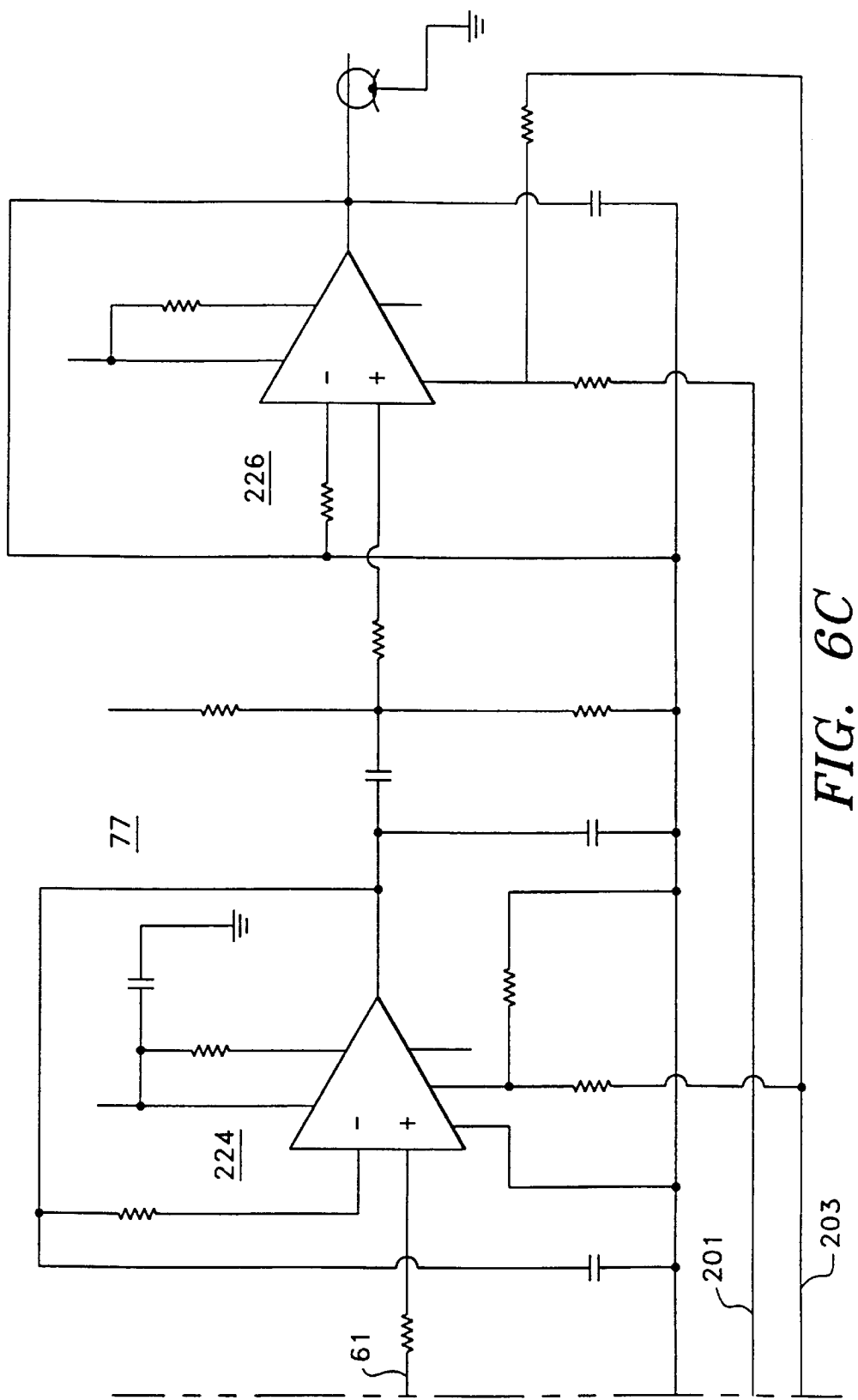

Referring now to FIGS. 6A, B, there is shown schematic representation 250. Schematic representation 250 is a more detailed representation of an embodiment of the system of the present invention including high discrimination ultrasonic measurement device 73. When crystal excitation pulse 83 on excitation line 42 is applied to transistor 45, transistor 45 turns on permitting capacitor 47 to discharge. When capacitor 47 discharges, transistor 49 is turned off causing gate transistor 43 to turn on.

When gate transistor 43 turns on, transistors 51 are turned on thereby supplying a reset to integrators 204, 212 of reset timer 200. The reset permits amplifiers 53, 55 of integrators 204, 212 to begin integrating. The output of amplifier 59, which receives the output of amplifier 55 of integration 212 is the quadratic polynomial previously described for approximating curve 132. The quadratic polynomial signal of amplifier 59 rides on a DC bias, with respect to line 57. The bias with respect to line 57 can be approximately two volts. Amplifier 66 removes the bias from the quadratic polynomial signal.

Line 61 of schematic representation 250 carries an electrical signal representative of the echo pulse of ultrasonic crystal 50 as previously described. The echo-representing signal of line 61 is applied to the input of amplifier 224 high discrimination circuitry 77. The output of amplifier 224 is applied to the input of amplifier 226. The gain of amplifiers 224, 226 is controlled by the quadratic polynomial of integrators 204, 212 by way of lines 201, 203.

Figure 7:
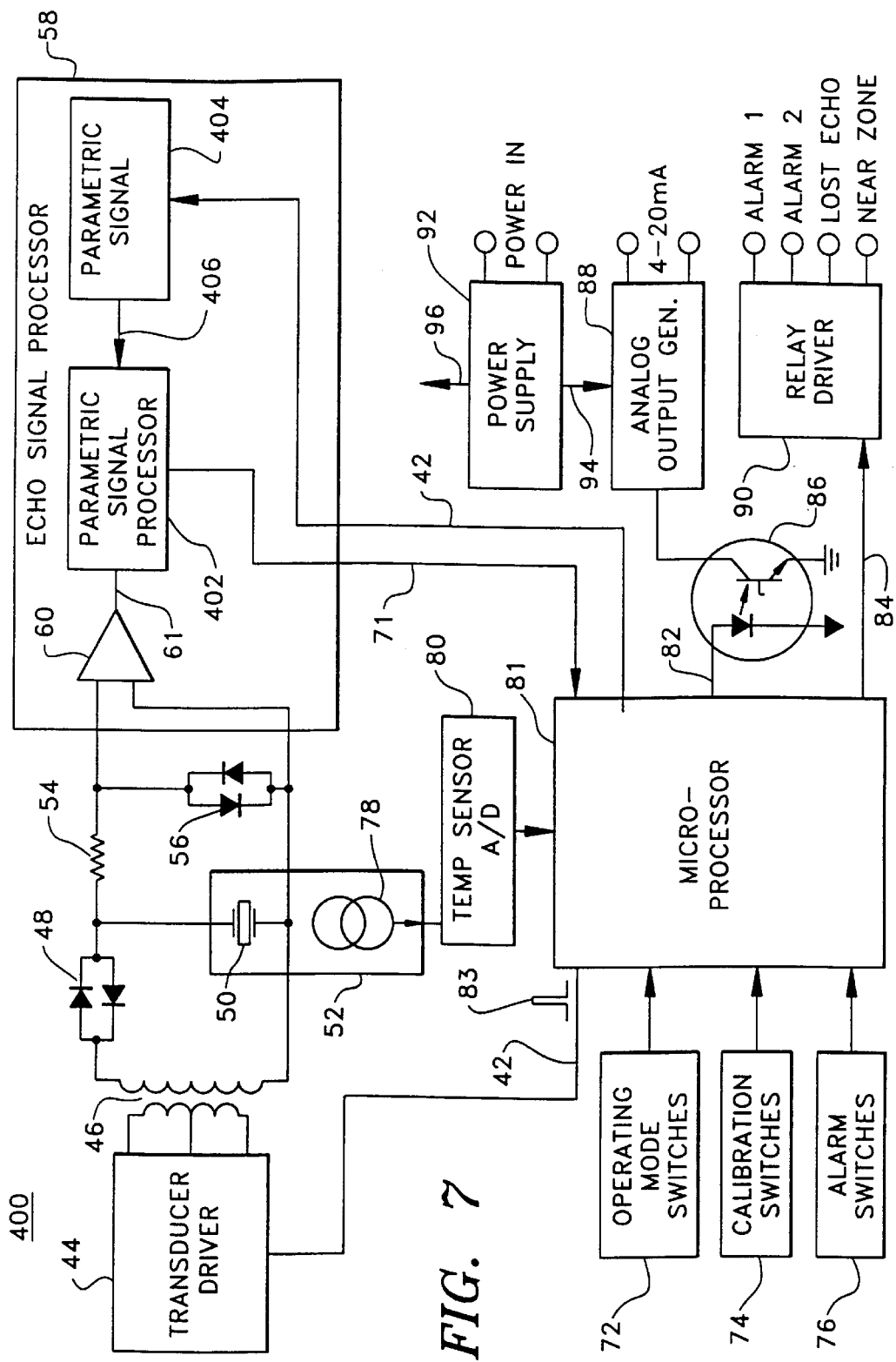
FIG. 7 is a block diagram representation of an alternate embodiment of the ultrasonic measurement instrument of FIG. 3 having a parametric signal processor and a parametric generator.

Referring now to FIG. 7, there is shown ultrasonic measurement system 400 of the present invention. Echo signal processor 58 of ultrasonic measurement system 400 is provided with parametric signal processor 402 and parameter generator 404 for making the sensitivity of system 400 constant with respect to the travel time of ultrasonic pulse 26. Software functions are performed within parameter generator 404 of measurement system 400 in order to provide parameters representative of the numerical approximation in accordance with curve 132 as previously described. The applying of the generated parameters by parameter generator 404 is controlled by microprocessor 81 by way of crystal excitation line 42.

Parametric system processor 402 receives the parameters generated in this manner from parameter generator 404 by way of line 406. The parameters generated by parameter generator 404, in accordance with the signals of excitation line 42, and applied to parametric signal processor 402, are effective to approximate the relationship illustrated by curve 132 of graphical representation 120 in substantially the same manner as disclosed with respect to ultrasonic measurement circuitry 77. Thus the amplitudes of the electrical signals representative of the echo signal of ultrasonic measurement instrument 400 are linearized with respect to pulse travel time.

Figure 8:
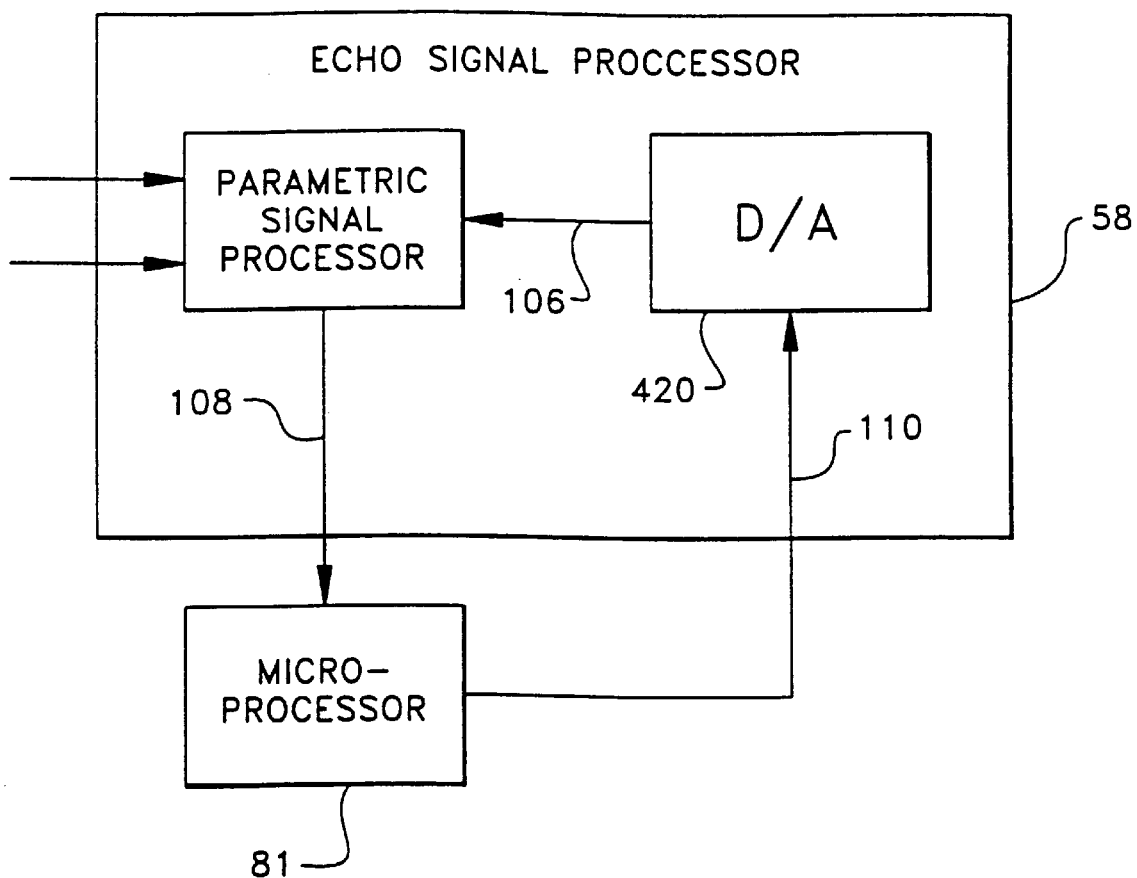
FIG. 8 is a block diagram representation of an alternate embodiment of the echo signal processor of the ultrasonic measurement instrument of FIG. 3.

Referring now to FIG. 8, there is shown an alternate embodiment of echo signal processor 58. In this embodiment of echo signal processor 58, microprocessor 81 performs the software functions necessary to provide the numerical approximation in accordance with curve 132 as previously described. The parameters generated in this manner are provided by microprocessor 81 in digital form on parameter lines 110. The digital parameters are applied to digital-to-analog converter 420 which converts them to analog form and applies them to parametric signal processor 402.

The analog parameters applied to parametric signal processor 402 by digital-to-analog converter 420 are effective to approximate the relationship illustrated by curve 132 of graphical representation 120 in substantially the same manner as disclosed with respect to circuitry 77. Thus the amplitudes of the electrical signals representative of the echo signals of an ultrasonic measuring system that includes the echo signal processor 58 of FIG. 8 can be made independent of the pulse travel time or the distance D.

Figure 9:
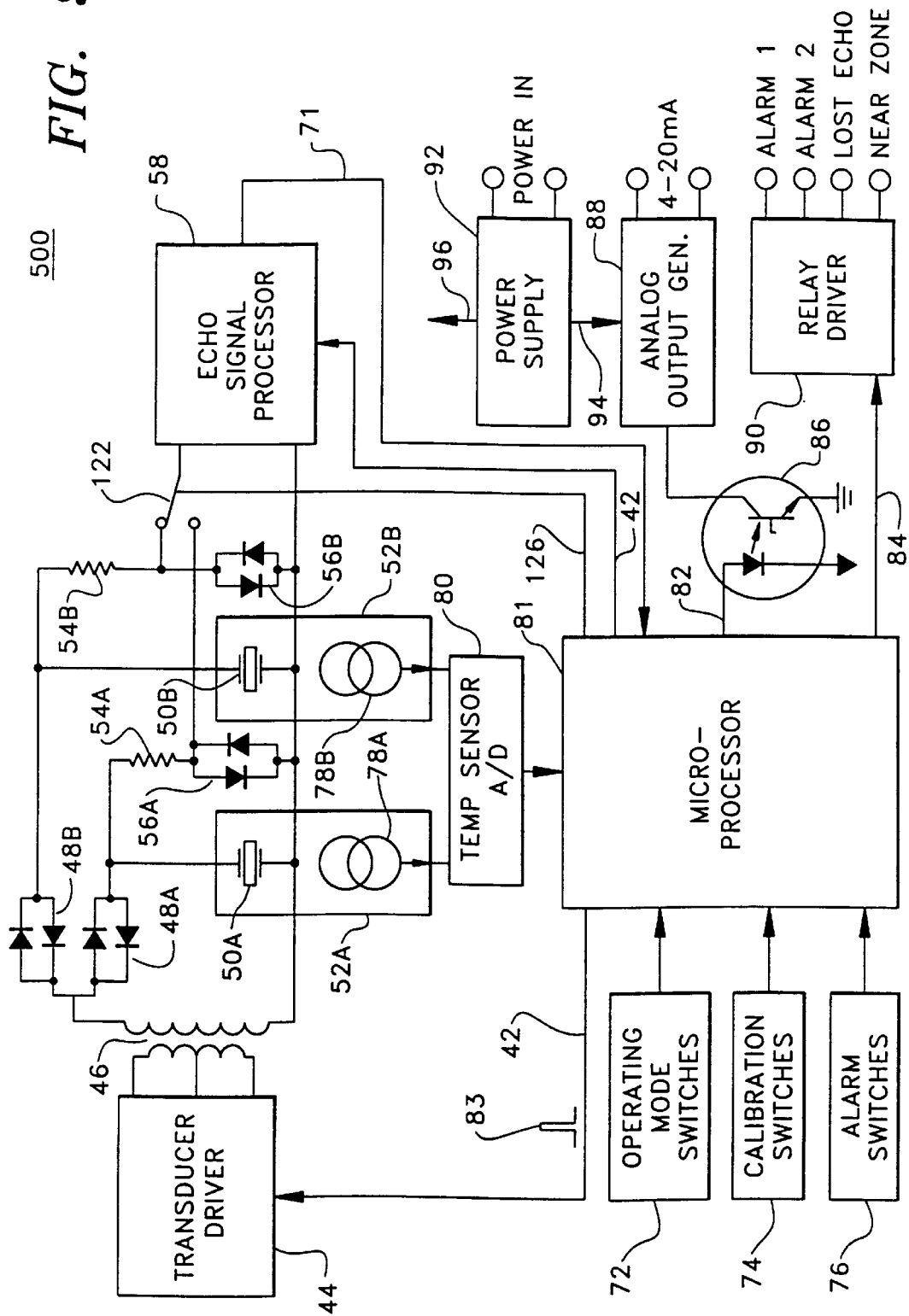
FIG. 9 is a block diagram representation of an alternate embodiment of the ultrasonic measurement system of FIG. 3 having dual ultrasonic transducers driven in parallel.

Referring now to FIG. 9, there is shown ultrasonic measurement system 500 of the present invention. Ultrasonic measurement system 500 is an alternate embodiment of ultrasonic measurement system 75 of the present invention. Two ultrasonic crystals 50a, b are provided in ultrasonic measurement system 500. Each ultrasonic crystal 50a, b of system 500 is included in a separate sensor 52a, b. Both ultrasonic crystals 50a, b are driven in response to microprocessor 81 by way of crystal excitation line 42 in the manner previously described with respect to ultrasonic measurement system 40. Furthermore, both ultrasonic crystals 50a, b are driven simultaneously and in parallel with each other in response to microprocessor 81. Thus, high voltage excitation pulse 83 at the output of transformer 46 is applied simultaneously to ultrasonic crystal 50a by way of diodes 48a and to ultrasonic crystal 50b by way of diodes 48b.

While crystals 58a, b are driven simultaneously within ultrasonic measurement system 500, the echo signals received by ultrasonic crystals 50a, b are processed separately. In order to perform the separate processing of the echo signals received by ultrasonic crystals 50a, b, ultrasonic measurement system 500 is provided with echo processor switch 122. Echo processor switch 122 operates under the control of microprocessor 81 by way of switch control line 126 to alternately apply the output of ultrasonic crystals 50a, b to echo system processor 58.

Figure 10:
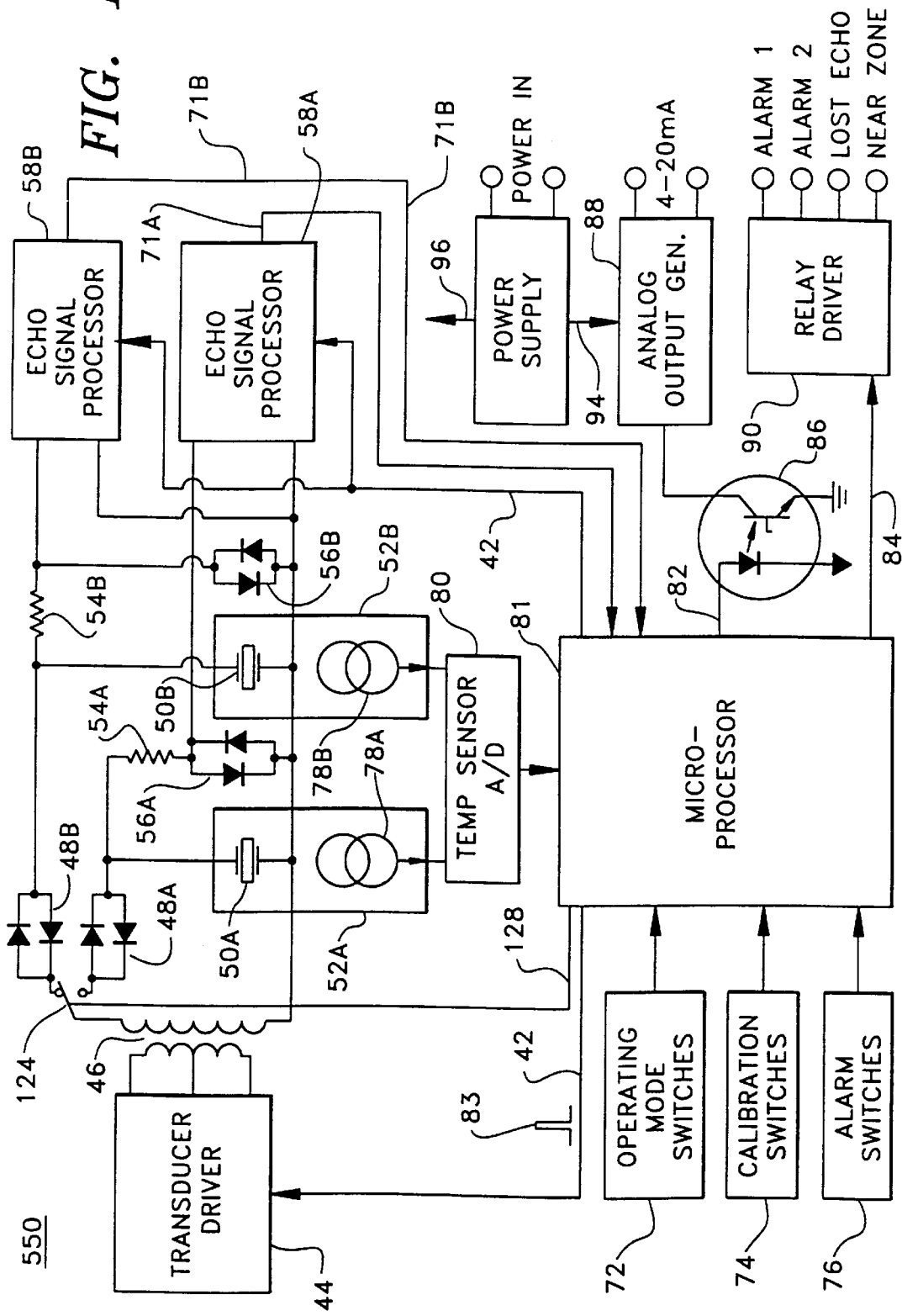
FIG. 10 is a block diagram representation of an alternate embodiment of the ultrasonic measurement system of FIG. 3 having dual ultrasonic transducers that are alternately driven.

Referring now to FIG. 10, there is shown ultrasonic measurement system 550 of the present invention. Ultrasonic measurement system 550 is provided with two sensors 52a, b, each having an ultrasonic crystal 50a, b. Ultrasonic crystals 50a, b of ultrasonic measurement system 550 are not driven simultaneously by microprocessor 81. Rather, excitation signals 83 from the secondary of transformer 46 of measurement system 550 are alternately applied to ultrasonic crystals 50a, b by excitation switch 124. Excitation switch 124 operates under the control of microprocessor 81 by way of switch control line 128. The outputs of crystals 50a, b, of ultrasonic measurement system 550, representative of echo signals within vessel 12, are applied to separate echo signal processors 58a, b.

Echo signal processor 58a receives the output of ultrasonic crystal 50a, by way of resistor 54a, clamped by diodes 56a. In accordance with this input, echo signal processor 58a provides a detect signal on detect line 71a. The detect signal on detect line 71a is applied to microprocessor 81.

Echo signal processor 58b receives the output of ultrasonic crystal 50b, by way of resistor 54b, clamped by diodes 56b. In accordance with this input, echo signal processor 58b provides a detect signal on detect line 71b. The detect signal on detect line 71b is applied to microprocessor 81.

Figure 11:
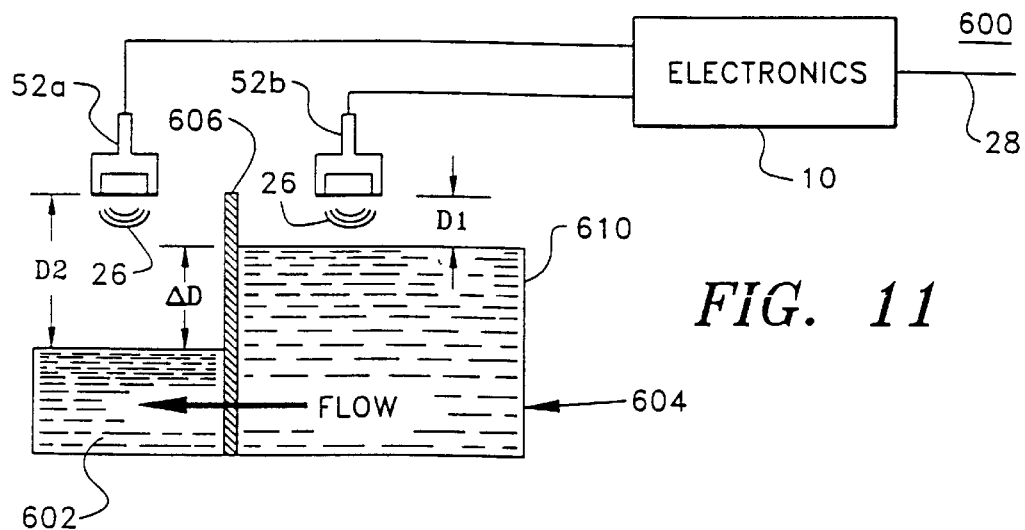
FIG. 11 is a block diagram representation of a system suitable for use with the ultrasonic measurement system of the present invention.

Referring now to FIG. 11, there is shown traveling screen ultrasonic measurement system 600. In traveling screen ultrasonic measurement system 600 a traveling screen 606 is inserted into water flow 604 in order to permit the water of water flow 604 to pass therethrough while preventing debris within the water from passing therethrough. Traveling screen 606 is moved under the control of ultrasonic measurement system 600 in order to remove debris which collects against traveling screen 606. Traveling screen ultrasonic measurement system 600 can be used, for example, at the water intake of a power plant or a water treatment system.

When debris collects against traveling screen 606 on the upstream side of traveling screen 606, water does not flow through traveling screen 606 as well as it flows when debris is removed. The collected debris causes the water level of upstream portion 610 of water flow 604 to rise to a higher level than the level of downstream portion 602. This causes a difference between the water levels of portions 610, 602 of water flow 604. When the difference between the levels of portions 610, 602 reaches a predetermined magnitude, traveling screen 606 can be moved to remove debris and permit better water flow therethrough.

In order to detect when the difference between the two water levels has reached the predetermined magnitude, two ultrasonic transducers 52a, b are provided in system 600. Ultrasonic transducer 52a detects distance D2. Distance D2 represents the water level of downstream portion 602. Ultrasonic transducer 52b detects the distance D1 of water flow 604. Distance D1 represents the water level of upstream portion 604. The difference between the two levels can be determined by subtracting distance D1 from distance D2.

It is understood by those skilled in the art that either ultrasonic measurement system 500 or ultrasonic measurement system 550 can be applied to traveling screen ultrasonic measurement system 600. When ultrasonic measurement system 500 is applied to measurement system 600, ultrasonic pulse 26 is applied to both downstream portion 602 of water flow 604 and upstream portion 610 of water flow 604 on every measurement cycle. The output signal on line 28 of traveling wave ultrasonic measurement system 600 alternately represents the received signals of sensors 52a, b on every other measurement cycle, as selected by echo processor switch 122. When ultrasonic measurement system 550 is applied to measurement system 600, sensors 52a, b alternately emit ultrasonic pulse 26 under the control of excitation control switch 124.

Figure 12:
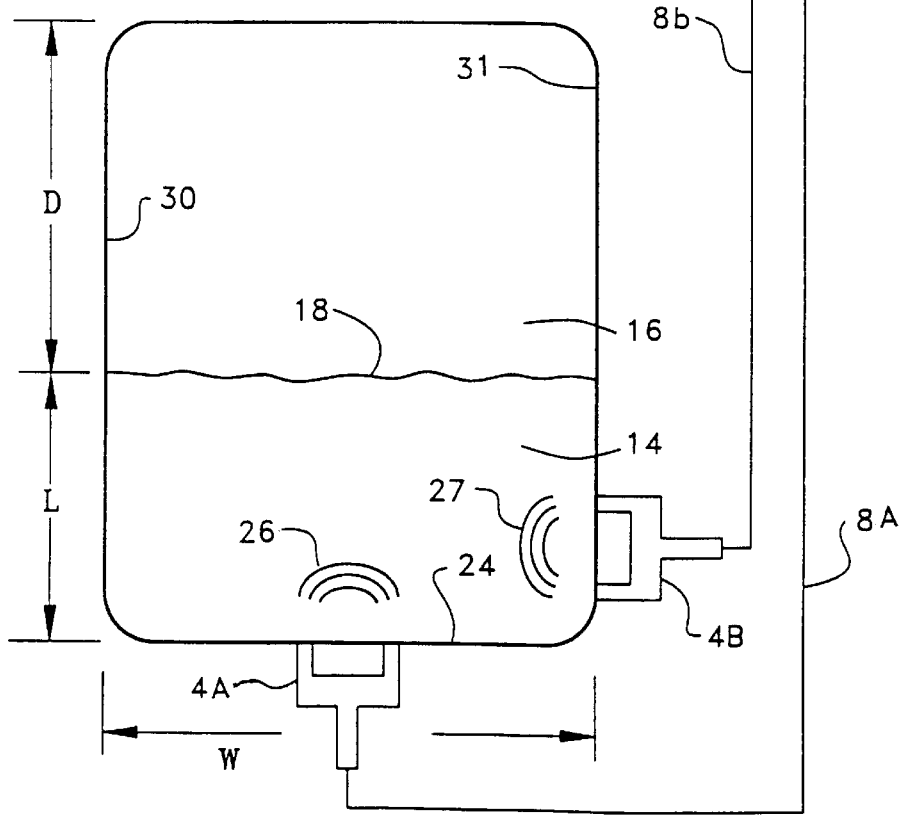
FIG. 12 is a block diagram representation of a system suitable for use with the ultrasonic measurement system of the present invention.

Referring now to FIG. 12, there is shown ultrasonic measurement system 650. Ultrasonic measurement system 650 is useful for compensating for changes in material 16 resulting in changes in the velocity of pulse 26 through material 16. In order to compensate for the effect of the velocity of material 16 on measurements performed by system 650, sensor 4b is provided on sidewall 30 of storage vessel 12. Additionally, sensor 4a is provided on vessel bottom 24.

Distance D of ultrasonic measurement system 650 can be calculated as the known reference distance from side to side in storage vessel 12, divided by the measured reference time for ultrasonic pulse 27 to travel from side to side of storage vessel 12, multiplied by the measured travel time T of ultrasonic pulse 26. The measurement of distance D using ultrasonic pulse 26 is thus compensated for changes in material 14. Ultrasonic measurement system 500 or ultrasonic measurement system 550 can be applied to ultrasonic measurement system 650. Ultrasonic measurement system 650 can be provided with a further ultrasonic transducer 4c in order to permit measurements to be taken from vessel bottom 24.

Figure 13:
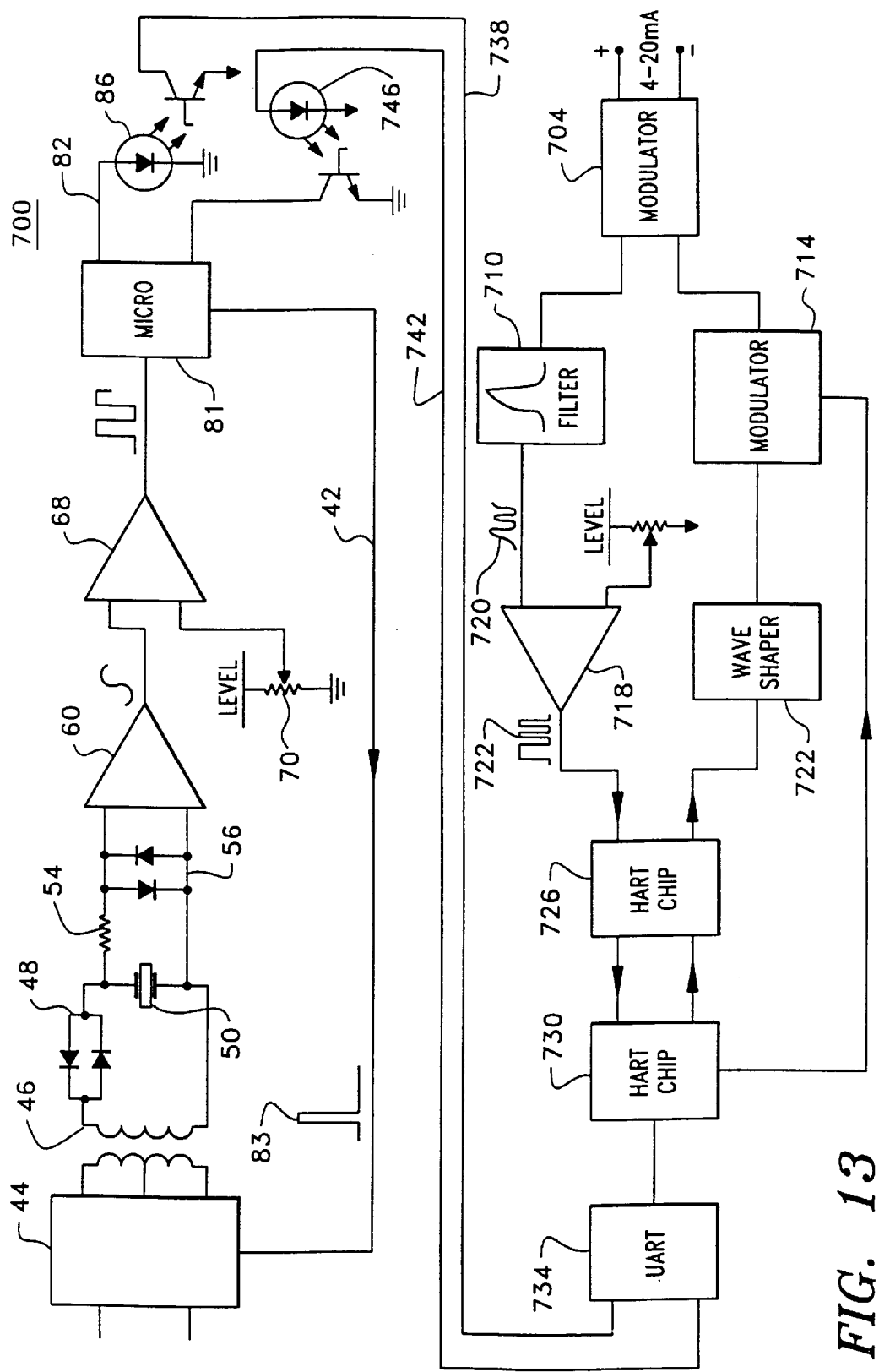
FIG. 13 is a block diagram representing an alternate embodiment of the ultrasonic measurement system of the present invention having monitoring input.

Referring now to FIG. 13, there is shown ultrasonic measurement system 700. Using ultrasonic measurement system 700, it is possible to perform data communication with microprocessor 81 by way of the same line used by system 700 for system output.

Port 705 of ultrasonic measurement system 700 can be used to provide the four milliamp to twenty milliamp measurement output signal in accordance with the method of the present invention as previously described. Additionally, data communication signals can be received and transmitted by way of port 705 as follows. The data communication signals are applied by modulator 704 to filter 710. The signals can be, for example, pulse modulation width signals.

Detector 720, in cooperation with threshold 719, provides a squared up signal 722 which is applied to HART 726 and, therefrom, to HART 730 in a conventional manner. The signal is then applied by UART 734 to microprocessor 81 by way of optoisolator 746. Signals from microprocessor 81, received by UART 734 by way of optoisolator 86, can be shaped and modulated by wave shaper 722 and modulator 714, respectively, prior to being applied to port 705. This permits remote interrogation and programming of microprocessor 81 by way of the measurement output line coupled to port 705.

Figure 14:
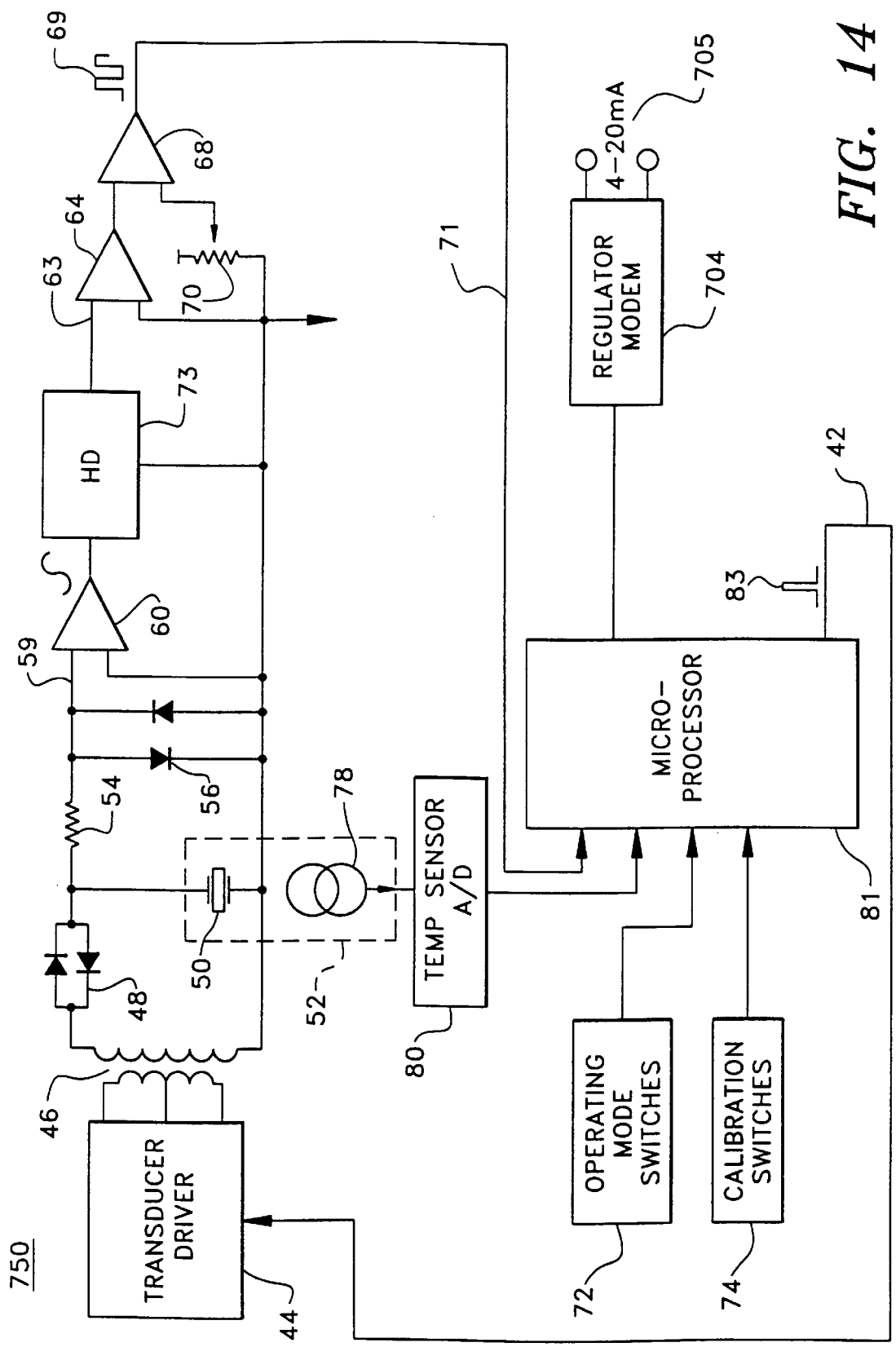
FIG. 14 is a block diagram representation of an alternate embodiment of the ultrasonic measurement system of the present invention.

Referring now to FIG. 14, there is shown ultrasonic measurement system 750. Ultrasonic measurement system 750 is an alternate embodiment of ultrasonic measurement systems 75, 400, 500, 550 and 700 that is suitable for two-wire operation. Both the application of a conventional dc voltage supply and the receiving of a measurement output signal can be performed at port 705 of ultrasonic measurement system 750 in a known manner. The voltage applied to port 705 of system 750 can be, for example, twenty-four volts. The measurement output signal at port 705 during two-wire operation of ultrasonic measurement system 750 is determined in accordance with the high discrimination ultrasonic measurement device 73 of the present invention.

Figure 15A:
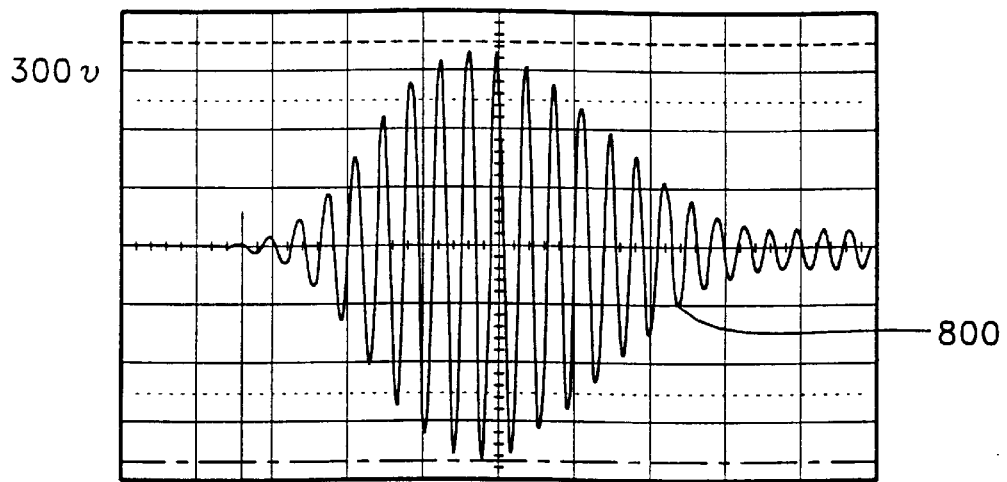
FIGS. 15A, B are curves representing tone bursts from an ultrasonic crystal.
Figure 15B:
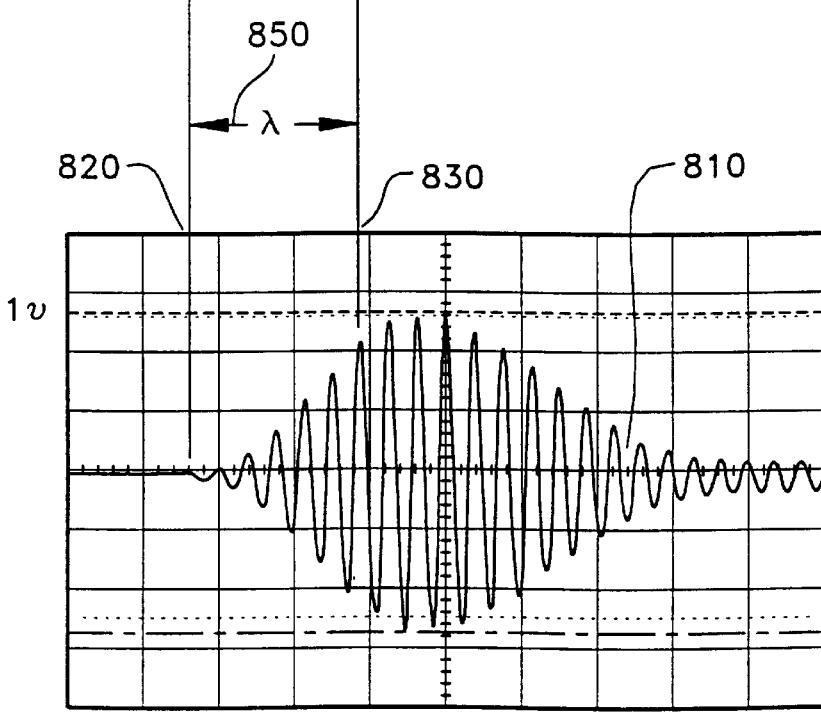

Referring now to FIGS. 15A, B there are shown curves 800, 810 representative of response tone bursts from ultrasonic crystal 50 for illustrating a manner in which the system of the present invention improves measurement linearity. Curve 800 represents a tone burst with a target one foot from transducer 6 and curve 810 represents a tone burst with a target thirty feet away. The system of the present invention improves measurement accuracy by eliminating spurious responses, in the manner previously described. Additionally, however, a source of non-linearity in the prior art due to detector 68 triggering at differing points within response bursts is eliminated by the present invention.

It is well understood by those skilled in the art that the response tone burst received by detector 68 varies with time over a substantial number of cycles as shown in curves 800, 810. Additionally, it is known that detector 68 triggers earlier in the curve for stronger responses and later in the curve for weaker responses. Thus reflections from shorter distances result in triggering earlier in the pulse and therefor cause non-linearity. For example, the trigger of curve 800 occurred at time 820 and the trigger of curve 810 occurred at time 830, for a difference of time 850. It is also understood that reflections from closer material surfaces 18 provide stronger responses.

In accordance with the present invention however the response signals from material surface 18 closer to transducer 6 are substantially the same strength as response signals from material signal 18 further away. Therefore, detector 68 triggers at the same point in the response curve regardless of distance D.

It will be understood that the frequency of the energy of ultrasonic pulse 26 of the material monitoring instruments of the present invention is usually higher than the twenty kilohertz upper frequency limit of human hearing. Therefore, such measurement instruments are typically referred to as ultrasonic measurement instruments. However, it will be understood by those skilled in the art that the method of the present invention can be used by measurement instruments emitting energy of any frequency suitable for determining the monitored parameters.

We claim:

1. An ultrasonic measurement method for use in an ultrasonic measurement system having an ultrasonic transducer, comprising the steps of:
   (a) emitting an ultrasonic pulse from an ultrasonic transducer;
   (b) receiving an ultrasonic pulse in accordance with a pulse travel time, wherein the amplitude of said received ultrasonic pulse varies according to said pulse travel time;
   (c) providing a first electrical signal representative of said received ultrasonic pulse;
   (d) applying variable amplification to said first electrical signal in accordance with said pulse travel time; and
   (e) providing a second electrical signal in accordance with said first electrical signal, wherein the amplitude of said second electrical signal is substantially independent of said pulse travel time during a time period corresponding to a range of said pulse travel time.

2. The ultrasonic measurement method of claim 1 comprising the step of determining said pulse travel time in accordance with a measurement of the duration of a time interval.

3. The ultrasonic measurement method of claim 2, comprising the step of measuring said duration of said time interval by measuring the time elapsed between said emitting and said receiving.

4. The ultrasonic measurement method of claim 3, comprising the step of determining a distance D in accordance with said pulse travel time.

5. The ultrasonic measurement method of claim 4, wherein the step of determining said distance D comprises determining said distance D in accordance with the relationship D=RT/2, wherein R is the speed of sound and T is said elapsed time.

6. The ultrasonic measurement method of claim 5, wherein said distance D is representative of the distance between said transducer and a material surface.

7. The ultrasonic measurement method of claim 6, comprising the step of determining a further distance in accordance with said determined distance D.

8. The ultrasonic measurement method of claim 7, wherein said further distance comprises the distance between a vessel bottom and said material surface.

9. The ultrasonic measurement method of claim 1, comprising the step of providing a gain control signal in accordance with said pulse travel time.

10. The ultrasonic measurement method of claim 9, comprising the step of applying said gain control signal to a variable amplifier.

11. The ultrasonic measurement method of claim 9, wherein said ultrasonic measurement system includes at least one integration device comprising the step of determining said gain control signal by integrating during said pulse travel time using said integration device.

12. The ultrasonic measurement method of claim 11, comprising the step of selectively applying constants to said integration device to provide measurement sensitivity substantially independent of said pulse travel time.

13. The ultrasonic measurement method of claim 9, comprising the step of providing a processor for providing said gain control signal.

14. The ultrasonic measurement method of claim 13, comprising the step of performing calculations by said processor to provide said gain control signal.

15. The ultrasonic measurement method of claim 13, comprising the step of performing table look ups by said processor to provide said gain control signal.

16. The ultrasonic measurement method of claim 1, comprising the step of applying a drive pulse to an ultrasonic transducer having an ultrasonic crystal for emitting said ultrasonic pulse.

17. An ultrasonic measurement method, comprising the steps of:
   (a) emitting an ultrasonic pulse from an ultrasonic transducer;
   (b) receiving an ultrasonic pulse in accordance with a pulse travel time, wherein the amplitude of said received ultrasonic pulse varies according to said pulse travel time;
   (c) providing a first electrical signal representative of said received ultrasonic pulse;
   (d) providing a gain control signal in accordance with said pulse travel time;
   (e) applying said gain control signal to a variable amplifier that amplifies the first electrical signal;
   (f) providing a second electrical signal in accordance with said first electrical signal, wherein the amplitude of said second electrical signal is substantially independent of said pulse travel time during a time period corresponding to a range of the pulse travel time; and
   (g) applying the output of said variable amplifier to a four to twenty amp indicator device.

18. The ultrasonic measurement method of claim 1, wherein said received ultrasonic pulse is formed by reflecting said emitted ultrasonic pulse off an object.

19. The ultrasonic measurement method of claim 18, wherein said object comprises a material surface.

20. An ultrasonic measurement method, comprising the steps of:
   (a) emitting an ultrasonic pulse from an ultrasonic transducer:
   (b) receiving an ultrasonic pulse in accordance with a pulse travel time, wherein the amplitude of said received ultrasonic pulse varies according to said pulse travel time;
   (c) providing a first electrical signal representative of said received ultrasonic pulse;
   (d) providing a gain control signal in accordance with said pulse travel time;
   (e) applying said gain control signal to cascaded variable amplifiers that amplify the first electrical signal; and
   (f) providing a second electrical signal in accordance with said first electrical signal, wherein the amplitude of said second electrical signal is substantially independent of said pulse travel time during a time period corresponding to a range of the pulse travel time.

21. The ultrasonic measurement method of claim 1, wherein said second electrical signal is applied to an analog-to-digital converter.

22. The ultrasonic measurement method of claim 1, wherein said emitted ultrasonic pulse is attenuated to provide said received ultrasonic pulse and step (d) compensates for said attenuating.

23. The ultrasonic measurement method of claim 1, wherein said method includes providing a plurality of ultrasonic transducers each transducer of said plurality of transducers emitting an ultrasonic pulse to provide a plurality of ultrasonic pulses.

24. The ultrasonic measurement method of claim 23, comprising the step of determining a plurality of distance measurements in accordance with said plurality of ultrasonic pulses.

25. The ultrasonic measurement method of claim 24, comprising the step of controlling a traveling gate in accordance with said plurality of distance measurements.

26. The ultrasonic measurement method of claim 24, comprising the step of determining a plurality of levels of a material surface in accordance with said plurality of distance measurements.

27. The ultrasonic measurement method of claim 1, comprising the step of emitting a plurality of ultrasonic pulses and determining the relationship between said pulse travel time and said amplitude of said first electrical signal for each pulse of said plurality of pulses.

28. The ultrasonic measurement method of claim 27, comprising the step of approximating said relationship to provide a plurality of correction parameters.

29. The ultrasonic measurement method of claim 28, wherein step (d) comprises the step of applying said correction parameters to said first electrical signal.

30. An ultrasonic measurement method, comprising the steps of:
   (a) emitting an ultrasonic pulse from an ultrasonic transducer;

(b) receiving an ultrasonic pulse in accordance with a pulse travel time, wherein the amplitude of said received pulse varies according to said pulse travel time;

(c) providing a first electrical signal representative of said received ultrasonic pulse;

(d) applying relatively lower amplification to said first electrical signal for relatively lower values of the pulse travel time and applying relatively larger amplification to said first electrical signal for relatively higher values of the pulse travel time; and (e) providing a second electrical signal in accordance with said first electrical signal, wherein the amplitude of the second electrical signal is substantially independent of said pulse travel time during a time period corresponding to a range of the pulse travel time.

31. An ultrasonic measurement method, comprising the steps of:

(a) emitting an ultrasonic pulse from an ultrasonic transducer;

(b) receiving an ultrasonic pulse in accordance with a pulse travel time, wherein the amplitude of said received ultrasonic pulse varies according to said pulse travel time;

(c) providing a first electrical signal representative of said received ultrasonic pulse;

(d) providing a gain control signal for amplification of the first electrical signal in accordance with said pulse travel time, wherein said gain control signal is determined by performing first and second integrations during said pulse travel time to provide first and second integration signals; and (e) providing a second electrical signal in accordance with said first electrical signal, wherein the amplitude of said second electrical signal is substantially independent of said pulse travel time during a time period corresponding to a range of the pulse travel time.

32. The ultrasonic measurement method of claim 31, wherein said first integration signal is proportional to said pulse travel time and said second integration signal is proportional to said pulse travel time squared.

33. The ultrasonic measurement method of claim 31, comprising the step of summing said first and second integration signals to form said gain control signal.

34. An ultrasonic measurement method, comprising the steps of:

(a) emitting an ultrasonic pulse from an ultrasonic transducer;

(b) receiving an ultrasonic pulse in accordance with a pulse travel time, wherein the amplitude of said received ultrasonic pulse varies according to said pulse travel time;

(c) providing a first electrical signal representative of said received ultrasonic pulse;

(d) providing a second electrical signal in accordance with said first electrical signal, wherein the amplitude of said second electrical signal is substantially independent of said pulse travel time during a time period corresponding to a range of the pulse travel time; wherein a level of a material is controlled in accordance with said second electrical signal.

35. An ultrasonic measurement method, comprising the steps of:

(a) emitting an ultrasonic pulse from an ultrasonic transducer;

(b) receiving an ultrasonic pulse in accordance with a pulse travel time, wherein the amplitude of said received ultrasonic pulse varies according to said pulse travel time, and the emitted ultrasonic pulse is attenuated to provide said received electronic pulse;

(c) providing a first electrical signal representative of said received ultrasonic pulse; and (d) providing a second electrical signal in accordance with said first electrical signal, wherein the amplitude of said second electrical signal is substantially independent of said pulse travel time during a time period corresponding to a range of the pulse travel time;

wherein step (d) compensates for said attenuating and said compensating includes compensating for humidity.

36. An ultrasonic measurement, comprising the steps of:

(a) emitting an ultrasonic pulse from an ultrasonic transducer;

(b) receiving an ultrasonic pulse in accordance with a pulse travel time, wherein the amplitude of said received ultrasonic pulse varies according to said pulse travel time;

(c) providing a first electrical signal representative of said received ultrasonic pulse;

(d) providing a second electrical signal in accordance with said first electrical signal, wherein the amplitude of said second electrical signal is substantially independent of said pulse travel time during a time period corresponding to a range of said pulse travel time; and (e) applying said second electrical signal to a two-wire measurement system.

37. An ultrasonic measurement method, comprising the steps of:

(a) emitting an ultrasonic pulse from an ultrasonic transducer;

(b) receiving an ultrasonic pulse in accordance with a pulse travel time, wherein the amplitude of said received ultrasonic pulse varies according to said pulse travel time;

(c) providing a first electrical signal representative of said received ultrasonic pulse and applying variable amplification to said first electrical signal in accordance with said pulse travel time;

(d) providing a second electrical signal in accordance with said first electrical signal, wherein the amplitude of said second electrical signal is substantially independent of said pulse travel time during a time period corresponding to a range of the pulse travel time; and (e) determining the level of a material in accordance with said second electrical signal.

38. An ultrasonic measurement system, comprising:

(a) means for emitting an ultrasonic pulse from an ultrasonic transducer;

(b) means for receiving an ultrasonic pulse in accordance with a pulse travel time, wherein the amplitude of said received ultrasonic pulse varies according to said pulse travel time;

(c) means for providing a first electrical signal representative of said received ultrasonic pulse and applying variable amplification to said first electrical signal in accordance with said pulse travel time;

(d) means for providing a second electrical signal in accordance with said first electrical signal, wherein the amplitude of said second electrical signal is substantially independent of said pulse travel time during a time period corresponding to a range of the pulse travel time; and (e) means for determining the level of a material in accordance with said second electrical signal.

39. An ultrasonic measurement system, comprising:

(a) an ultrasonic transducer that emits an ultrasonic pulse;

(b) a receiver that receives an ultrasonic pulse in accordance with a pulse travel time, wherein the amplitude of said received ultrasonic pulse varies according to said pulse travel time;

(c) signal processing circuitry, coupled to the receiver, that provides a first electrical signal representative of said received ultrasonic pulse and a second electrical signal in accordance with said first electrical signal, wherein the amplitude of said second electrical signal is substantially independent of said pulse travel time during a time period corresponding to a range of the pulse travel time; and (d) a microprocessor that determines the level of a material in accordance with said second electrical signal.

40. The system of claim 39, wherein the receiver is integral with the ultrasonic transducer.

41. An ultrasonic measurement system having an ultrasonic transducer, comprising:

(a) means for emitting an ultrasonic pulse from said ultrasonic transducer;

(b) means for receiving an ultrasonic pulse in accordance with a pulse travel time, wherein the amplitude of said received ultrasonic pulse varies according to said pulse travel time;

(c) signal processing circuitry that provides a first electrical signal representative of said received ultrasonic pulse, applies variable amplification to said first electrical signal in accordance with said pulse travel time, and provides a second electrical signal in accordance with said first electrical signal, wherein the amplitude of said second electrical signal is substantially independent of said pulse travel time during a time period corresponding to a range of said pulse travel time.

42. The system of claim 41, wherein the receiver is integral with the ultrasonic transducer.

* * * * *